(12) United States Patent
Bracken et al.

(10) Patent No.: US 9,993,619 B2
(45) Date of Patent: Jun. 12, 2018

(54) SECUREMENT SYSTEM FOR A MEDICAL ARTICLE

(75) Inventors: Ronald L. Bracken, Monroe, GA (US); Vasu Nishtala, Snellville, GA (US); Larry White, Duluth, GA (US); Robert Young, Loganville, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 949 days.

(21) Appl. No.: 12/175,351

(22) Filed: Jul. 17, 2008

(65) Prior Publication Data
US 2009/0143742 A1 Jun. 4, 2009

Related U.S. Application Data

(60) Provisional application No. 60/950,225, filed on Jul. 17, 2007.

(51) Int. Cl.
*A61M 25/02* (2006.01)
*A61M 5/14* (2006.01)

(52) U.S. Cl.
CPC .......... *A61M 25/02* (2013.01); *A61M 5/1418* (2013.01); *A61M 2025/024* (2013.01); *A61M 2025/028* (2013.01)

(58) Field of Classification Search
CPC ............ A61M 25/02; A61M 2025/024; A61M 2025/0246; A61M 2025/0253; A61M 39/1011; A51M 2025/028
USPC .......................................... 604/174, 176–180
See application file for complete search history.

(56) References Cited

U.S. PATENT DOCUMENTS

| | | | |
|---|---|---|---|
| 2,402,306 A | 6/1946 | Turkel |
| 2,525,398 A | 10/1950 | Collins |
| 2,533,961 A | 12/1950 | Rousseau et al. |
| 2,707,953 A | 5/1955 | Ryan |
| 3,046,984 A | 7/1962 | Eby |
| 3,059,645 A | 10/1962 | Hasbrouck et al. |
| 3,064,648 A | 11/1962 | Bujan |
| 3,167,072 A | 1/1965 | Stone et al. |
| 3,194,235 A | 7/1965 | Cooke |
| 3,245,567 A | 4/1966 | Knight |

(Continued)

FOREIGN PATENT DOCUMENTS

| | | |
|---|---|---|
| CA | 1311977 C | 12/1992 |
| CA | 1318824 C | 6/1993 |

(Continued)

OTHER PUBLICATIONS

Search Result, Percufix® Catheter Cuff Kit, downloaded from the Internet on Aug. 15, 2001.

(Continued)

*Primary Examiner* — Lauren P Farrar
(74) *Attorney, Agent, or Firm* — Rutan & Tucker, LLP

(57) ABSTRACT

A securement system for anchoring a medical article to a patient includes a pliant holding device. The device has a body and a plurality of tentacles extending from the body. The tentacles compress and may conform around at least a portion of the medical article to form a secure mount. The holding device may also cushion the medical article and protect the site of attachment on the patient while promoting air circulation. The holding device may include a support and a hinge so that the holding device may be swung away from the medical article to provide easy access for a medical provider.

21 Claims, 25 Drawing Sheets

(56) References Cited

U.S. PATENT DOCUMENTS

| | | |
|---|---|---|
| 3,288,137 A | 11/1966 | Lund |
| 3,394,954 A | 7/1968 | Sams |
| 3,482,569 A | 12/1969 | Raaelli, Sr. |
| 3,529,597 A | 9/1970 | Fuzak |
| 3,589,361 A | 6/1971 | Loper et al. |
| 3,602,227 A | 8/1971 | Andrew |
| 3,613,663 A | 10/1971 | Johnson |
| 3,630,195 A | 12/1971 | Santomieri |
| 3,677,250 A | 7/1972 | Thomas |
| 3,686,896 A | 8/1972 | Rutter |
| 3,766,915 A | 10/1973 | Rychlik |
| 3,782,383 A | 1/1974 | Thompson et al. |
| 3,812,851 A | 5/1974 | Rodriguez |
| 3,826,254 A | 7/1974 | Mellor |
| 3,834,380 A | 9/1974 | Boyd |
| 3,856,020 A | 12/1974 | Kovac |
| 3,863,527 A | 2/1975 | Benning |
| 3,863,631 A | 2/1975 | Baldwin |
| 3,900,026 A | 8/1975 | Wagner |
| 3,901,226 A | 8/1975 | Scardenzan |
| 3,906,946 A | 9/1975 | Nordstrom |
| 3,920,001 A | 11/1975 | Edwards |
| 3,942,228 A | 3/1976 | Buckman et al. |
| 3,973,565 A | 8/1976 | Steer |
| 3,993,081 A | 11/1976 | Cussell |
| 4,004,586 A | 1/1977 | Christensen et al. |
| D243,477 S | 2/1977 | Cutruzzula et al. |
| 4,020,835 A | 5/1977 | Nordstrom et al. |
| 4,037,599 A | 7/1977 | Raulerson |
| 4,057,066 A | 11/1977 | Taylor |
| 4,059,105 A | 11/1977 | Cutruzzula et al. |
| 4,079,738 A | 3/1978 | Dunn et al. |
| 4,082,094 A | 4/1978 | Dailey |
| 4,114,618 A | 9/1978 | Vargas |
| 4,116,196 A | 9/1978 | Kaplan et al. |
| 4,123,091 A | 10/1978 | Cosentino et al. |
| 4,129,128 A | 12/1978 | McFarlane |
| 4,133,312 A | 1/1979 | Burd |
| 4,142,527 A | 3/1979 | Garcia |
| 4,161,177 A | 7/1979 | Fuchs |
| 4,165,748 A | 8/1979 | Johnson |
| D252,822 S | 9/1979 | McFarlane |
| 4,170,993 A | 10/1979 | Alvarez |
| 4,170,995 A | 10/1979 | Levine et al. |
| 4,182,455 A | 1/1980 | Zurawin |
| 4,193,174 A | 3/1980 | Stephens |
| 4,194,504 A | 3/1980 | Harms et al. |
| D256,162 S | 7/1980 | Haerr et al. |
| 4,224,937 A | 9/1980 | Gordon |
| 4,230,109 A | 10/1980 | Geiss |
| 4,248,229 A | 2/1981 | Miller |
| 4,250,880 A | 2/1981 | Gordon |
| 4,275,721 A | 6/1981 | Olson |
| 4,284,076 A | 8/1981 | Hall |
| 4,314,568 A | 2/1982 | Loving |
| 4,316,461 A | 2/1982 | Marais et al. |
| 4,324,236 A | 4/1982 | Gordon et al. |
| 4,326,519 A | 4/1982 | D'Alo et al. |
| 4,333,468 A | 6/1982 | Geist |
| 4,356,599 A | 11/1982 | Larson et al. |
| 4,362,156 A | 12/1982 | Feller, Jr. et al. |
| 4,389,754 A | 6/1983 | Kogyo |
| 4,392,853 A | 7/1983 | Muto |
| 4,397,647 A | 8/1983 | Gordon |
| 4,398,757 A | 8/1983 | Floyd et al. |
| 4,405,163 A | 9/1983 | Voges et al. |
| 4,405,312 A | 9/1983 | Gross et al. |
| 4,435,174 A | 3/1984 | Redmond et al. |
| 4,435,175 A | 3/1984 | Friden |
| 4,439,193 A | 3/1984 | Larkin |
| D273,993 S | 5/1984 | Schulte et al. |
| 4,449,975 A | 5/1984 | Perry |
| 4,453,933 A | 6/1984 | Speaker |
| 4,470,410 A | 9/1984 | Elliott |
| 4,474,559 A | 10/1984 | Steiger |
| 4,480,639 A | 11/1984 | Peterson et al. |
| 4,484,913 A | 11/1984 | Swauger |
| 4,500,338 A | 2/1985 | Young et al. |
| 4,516,968 A | 5/1985 | Marshall et al. |
| 4,517,971 A | 5/1985 | Sorbonne |
| 4,533,349 A | 8/1985 | Bark |
| 4,561,857 A | 12/1985 | Sacks |
| 4,563,177 A | 1/1986 | Kamen |
| 4,583,976 A * | 4/1986 | Ferguson .................. 604/174 |
| 4,585,435 A | 4/1986 | Vaillancourt |
| 4,585,444 A | 4/1986 | Harris |
| 4,621,029 A | 11/1986 | Kawaguchi |
| 4,623,102 A | 11/1986 | Hough, Jr. |
| 4,627,842 A | 12/1986 | Katz |
| 4,631,056 A | 12/1986 | Dye |
| 4,632,670 A | 12/1986 | Mueller, Jr. |
| 4,633,863 A | 1/1987 | Filips et al. |
| 4,636,552 A | 1/1987 | Gay et al. |
| 4,645,492 A | 2/1987 | Weeks |
| 4,650,473 A | 3/1987 | Bartholomew et al. |
| 4,659,329 A | 4/1987 | Annis |
| 4,660,555 A | 4/1987 | Payton |
| 4,666,434 A | 5/1987 | Kaufman |
| 4,669,458 A | 6/1987 | Abraham et al. |
| 4,683,882 A | 8/1987 | Laird |
| 4,693,710 A | 9/1987 | McCool |
| 4,699,616 A | 10/1987 | Nowak et al. |
| 4,711,636 A | 12/1987 | Bierman |
| 4,723,948 A | 2/1988 | Clark et al. |
| 4,733,666 A | 3/1988 | Mercer, Jr. |
| 4,737,143 A | 4/1988 | Russell |
| 4,742,824 A | 5/1988 | Payton et al. |
| 4,743,231 A | 5/1988 | Kay et al. |
| 4,752,292 A | 6/1988 | Lopez et al. |
| 4,775,121 A | 10/1988 | Carly |
| 4,792,163 A | 12/1988 | Kulle |
| 4,795,429 A | 1/1989 | Feldstein |
| 4,808,162 A | 2/1989 | Oliver |
| 4,822,342 A | 4/1989 | Brawner |
| 4,826,486 A | 5/1989 | Palsrok et al. |
| 4,832,019 A | 5/1989 | Weinstein et al. |
| 4,834,702 A | 5/1989 | Rocco |
| 4,834,716 A | 5/1989 | Ogle, II |
| 4,838,858 A | 6/1989 | Wortham et al. |
| D302,304 S | 7/1989 | Kulle et al. |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,878,897 A | 11/1989 | Katzin |
| 4,880,412 A | 11/1989 | Weiss |
| 4,897,082 A | 1/1990 | Erskine |
| 4,898,587 A | 2/1990 | Mera |
| 4,919,654 A | 4/1990 | Kalt |
| 4,921,199 A | 5/1990 | Villaveces |
| 4,932,943 A | 6/1990 | Nowak |
| 4,934,375 A | 6/1990 | Cole et al. |
| 4,941,882 A | 7/1990 | Ward et al. |
| 4,955,864 A | 9/1990 | Hajduch |
| 4,961,505 A | 10/1990 | Moeller |
| 4,966,582 A | 10/1990 | Sit et al. |
| 4,976,700 A | 12/1990 | Tollini |
| 4,981,469 A | 1/1991 | Whitehouse et al. |
| 4,981,475 A | 1/1991 | Haindl |
| 4,986,815 A | 1/1991 | Schneider |
| 4,997,421 A | 3/1991 | Palsrok et al. |
| 5,024,665 A | 6/1991 | Kaufman |
| 5,037,397 A * | 8/1991 | Kalt et al. .................. 604/174 |
| 5,037,398 A | 8/1991 | Buchanan |
| 5,037,405 A | 8/1991 | Crosby |
| 5,069,206 A | 12/1991 | Crosbie |
| 5,073,170 A | 12/1991 | Schneider |
| 5,074,847 A | 12/1991 | Greenwell et al. |
| D323,390 S | 1/1992 | Paine et al. |
| 5,084,026 A | 1/1992 | Shapiro |
| 5,098,048 A | 3/1992 | Chen |
| 5,098,399 A | 3/1992 | Tollini |
| 5,105,807 A | 4/1992 | Kahn et al. |
| 5,112,313 A | 5/1992 | Sallee |

(56) References Cited

U.S. PATENT DOCUMENTS

| | | | |
|---|---|---|---|
| 5,116,324 A | 5/1992 | Brierley et al. | |
| 5,120,320 A | 6/1992 | Fayngold | |
| 5,135,506 A | 8/1992 | Gentelia et al. | |
| 5,137,519 A | 8/1992 | Littrell et al. | |
| 5,147,322 A | 9/1992 | Bowen et al. | |
| 5,156,641 A | 10/1992 | White | |
| 5,192,273 A | 3/1993 | Bierman et al. | |
| 5,192,274 A | 3/1993 | Bierman | |
| 5,195,981 A | 3/1993 | Johnson | |
| 5,215,532 A | 6/1993 | Atkinson | |
| 5,226,892 A | 7/1993 | Boswell | |
| 5,236,421 A | 8/1993 | Becher | |
| 5,238,010 A | 8/1993 | Grabenkort et al. | |
| 5,248,306 A | 9/1993 | Clark et al. | |
| 5,263,943 A | 11/1993 | Vanderbrook | |
| 5,266,401 A | 11/1993 | Tollini | |
| 5,267,967 A | 12/1993 | Schneider | |
| 5,279,578 A | 1/1994 | Cooke | |
| 5,290,248 A | 3/1994 | Bierman et al. | |
| 5,292,013 A | 3/1994 | Earl | |
| 5,292,312 A | 3/1994 | Delk et al. | |
| 5,304,146 A | 4/1994 | Johnson et al. | |
| 5,306,243 A | 4/1994 | Bonaldo | |
| D347,060 S | 5/1994 | Bierman | |
| 5,308,337 A | 5/1994 | Bingisser | |
| 5,314,411 A | 5/1994 | Bierman et al. | |
| 5,322,097 A | 6/1994 | Wright | |
| 5,328,487 A | 7/1994 | Starchevich | |
| 5,334,186 A | 8/1994 | Alexander | |
| 5,336,195 A | 8/1994 | Daneshvar | |
| 5,338,308 A | 8/1994 | Wilk | |
| 5,342,317 A | 8/1994 | Claywell | |
| 5,344,406 A | 9/1994 | Spooner | |
| 5,344,414 A | 9/1994 | Lopez et al. | |
| 5,352,211 A * | 10/1994 | Merskelly | 604/180 |
| 5,354,282 A | 10/1994 | Bierman | |
| 5,356,379 A | 10/1994 | Vaillancourt | |
| 5,356,391 A | 10/1994 | Stewart | |
| 5,370,627 A | 12/1994 | Conway | |
| 5,372,589 A | 12/1994 | Davis | |
| 5,380,293 A | 1/1995 | Grant | |
| 5,380,294 A | 1/1995 | Persson | |
| 5,380,301 A | 1/1995 | Prichard et al. | |
| 5,380,395 A | 1/1995 | Uchida | |
| 5,382,239 A | 1/1995 | Orr et al. | |
| 5,382,240 A | 1/1995 | Lam | |
| 5,389,082 A | 2/1995 | Baugues et al. | |
| 5,395,344 A | 3/1995 | Beisang, III et al. | |
| 5,402,776 A | 4/1995 | Islava | |
| 5,403,285 A | 4/1995 | Roberts | |
| 5,413,120 A | 5/1995 | Grant | |
| 5,413,562 A | 5/1995 | Swauger | |
| D359,120 S | 6/1995 | Sallee et al. | |
| 5,443,460 A | 8/1995 | Miklusek | |
| 5,449,344 A | 9/1995 | Taylor et al. | |
| 5,456,671 A | 10/1995 | Bierman | |
| 5,468,231 A | 11/1995 | Newman et al. | |
| 5,470,321 A | 11/1995 | Forster et al. | |
| D364,922 S | 12/1995 | Bierman | |
| 5,484,420 A | 1/1996 | Russo | |
| 5,484,425 A | 1/1996 | Fischell et al. | |
| 5,494,245 A | 2/1996 | Suzuki et al. | |
| 5,496,282 A | 3/1996 | Militzer et al. | |
| 5,496,283 A | 3/1996 | Alexander | |
| 5,498,241 A | 3/1996 | Fabozzi | |
| 5,499,976 A | 3/1996 | Dalton | |
| 5,507,535 A | 4/1996 | McKamey et al. | |
| 5,520,656 A | 5/1996 | Byrd | |
| 5,522,803 A | 6/1996 | Teissen-Simony | |
| 5,527,293 A | 6/1996 | Lamierowski | |
| 5,531,695 A | 7/1996 | Swisher | |
| 5,539,020 A | 7/1996 | Bracken et al. | |
| 5,549,567 A | 8/1996 | Wolman | |
| 5,551,421 A | 9/1996 | Noureldin et al. | |
| D375,355 S | 11/1996 | Bierman | |
| 5,577,516 A | 11/1996 | Schaeffer | |
| 5,578,013 A | 11/1996 | Bierman | |
| 5,593,395 A | 1/1997 | Martz | |
| 5,605,546 A | 2/1997 | Wolzinger et al. | |
| 5,620,427 A | 4/1997 | Werschmidt et al. | |
| 5,626,565 A | 5/1997 | Landis et al. | |
| 5,637,098 A | 6/1997 | Bierman | |
| 5,643,217 A | 7/1997 | Dobkin | |
| 5,664,581 A | 9/1997 | Ashley | |
| 5,681,290 A | 10/1997 | Alexander | |
| 5,685,859 A | 11/1997 | Kornerup | |
| 5,686,096 A | 11/1997 | Khan et al. | |
| 5,690,616 A | 11/1997 | Mogg | |
| 5,690,617 A | 11/1997 | Wright | |
| 5,693,032 A | 12/1997 | Bierman | |
| 5,702,371 A | 12/1997 | Bierman | |
| D389,911 S | 1/1998 | Bierman | |
| 5,722,959 A | 3/1998 | Bierman | |
| 5,728,053 A | 3/1998 | Calvert | |
| 5,755,225 A | 5/1998 | Hutson | |
| 5,776,106 A | 7/1998 | Matyas | |
| 5,800,402 A | 9/1998 | Bierman | |
| 5,800,410 A | 9/1998 | Gawreluk | |
| 5,810,781 A | 9/1998 | Bierman | |
| D399,954 S | 10/1998 | Bierman | |
| 5,827,230 A | 10/1998 | Bierman | |
| 5,827,239 A | 10/1998 | Dillon et al. | |
| 5,833,666 A | 11/1998 | Davis et al. | |
| 5,833,667 A | 11/1998 | Bierman | |
| 5,846,255 A | 12/1998 | Casey | |
| 5,855,591 A | 1/1999 | Bierman | |
| 5,885,251 A | 3/1999 | Luther | |
| 5,885,254 A | 3/1999 | Matyas | |
| 5,897,519 A | 4/1999 | Shesol et al. | |
| 5,911,707 A | 6/1999 | Wolvek et al. | |
| 5,916,199 A | 6/1999 | Miles | |
| 5,922,470 A | 7/1999 | Bracken et al. | |
| 5,944,696 A | 8/1999 | Bayless et al. | |
| 5,947,931 A | 9/1999 | Bierman | |
| 6,015,119 A | 1/2000 | Starchevich | |
| 6,050,934 A | 4/2000 | Mikhail et al. | |
| 6,054,523 A | 4/2000 | Braun et al. | |
| D425,619 S | 5/2000 | Bierman | |
| 6,058,574 A | 5/2000 | Facey et al. | |
| 6,067,985 A | 5/2000 | Islava | |
| 6,099,509 A | 8/2000 | Brown, Jr. et al. | |
| 6,113,577 A | 9/2000 | Hakky et al. | |
| 6,131,575 A | 10/2000 | Lenker et al. | |
| 6,132,398 A | 10/2000 | Bierman | |
| 6,132,399 A | 10/2000 | Shultz | |
| D433,503 S | 11/2000 | Powers et al. | |
| 6,206,897 B1 | 3/2001 | Jamiolkowski et al. | |
| 6,213,979 B1 * | 4/2001 | Bierman | 604/174 |
| 6,213,996 B1 | 4/2001 | Jepson et al. | |
| 6,216,885 B1 | 4/2001 | Guillaume | |
| 6,224,571 B1 | 5/2001 | Bierman | |
| 6,228,064 B1 | 5/2001 | Abita et al. | |
| 6,231,547 B1 | 5/2001 | O'Hara | |
| 6,231,548 B1 | 5/2001 | Bassett | |
| 6,234,465 B1 | 5/2001 | Sutton, Jr. | |
| 6,258,066 B1 | 7/2001 | Urich | |
| 6,273,873 B1 | 8/2001 | Fleischer | |
| 6,283,945 B1 | 9/2001 | Bierman | |
| 6,287,281 B1 | 9/2001 | Nishtala et al. | |
| 6,290,676 B1 | 9/2001 | Bierman | |
| 6,332,874 B1 | 12/2001 | Eliasen et al. | |
| 6,361,523 B1 | 3/2002 | Bierman | |
| 6,375,639 B1 | 4/2002 | Duplessie et al. | |
| 6,387,075 B1 | 5/2002 | Stivland et al. | |
| 6,387,076 B1 * | 5/2002 | Landuyt | A61M 25/02 128/DIG. 6 |
| 6,413,240 B1 | 7/2002 | Bierman et al. | |
| 6,428,515 B1 | 8/2002 | Bierman et al. | |
| 6,428,516 B1 | 8/2002 | Bierman | |
| 6,436,073 B1 | 8/2002 | Von Teichert | |
| 6,447,485 B2 | 9/2002 | Bierman | |
| 6,447,486 B1 | 9/2002 | Tollini | |
| 6,471,676 B1 | 10/2002 | DeLegge et al. | |
| 6,482,183 B1 | 11/2002 | Pausch et al. | |

(56) References Cited

U.S. PATENT DOCUMENTS

| | | |
|---|---|---|
| 6,488,664 B1 | 12/2002 | Solomon et al. |
| 6,491,664 B2 | 12/2002 | Bierman |
| 6,500,154 B1 | 12/2002 | Hakky et al. |
| D469,530 S | 1/2003 | Gomez |
| 6,517,522 B1 | 2/2003 | Bell et al. |
| 6,551,285 B1 | 4/2003 | Bierman |
| 6,572,588 B1 | 6/2003 | Bierman et al. |
| 6,582,403 B1 | 6/2003 | Bierman et al. |
| 6,596,402 B2 | 7/2003 | Sorens et al. |
| 6,616,635 B1 | 9/2003 | Bell et al. |
| 6,626,890 B2 | 9/2003 | Nguyen et al. |
| 6,652,487 B1 | 11/2003 | Cook |
| 6,663,600 B2 | 12/2003 | Bierman et al. |
| 6,673,046 B2 | 1/2004 | Bierman et al. |
| 6,689,104 B2 | 2/2004 | Bierman |
| 6,703,120 B1 | 3/2004 | Ko et al. |
| 6,770,055 B2 | 8/2004 | Bierman et al. |
| 6,786,892 B2 | 9/2004 | Bierman |
| 6,809,230 B2 | 10/2004 | Hancock et al. |
| 6,827,705 B2 | 12/2004 | Bierman |
| 6,827,706 B2 | 12/2004 | Tollini |
| 6,827,707 B2 | 12/2004 | Wright et al. |
| 6,834,652 B2 | 12/2004 | Altman |
| 6,837,875 B1 | 1/2005 | Bierman |
| 6,866,652 B2 | 3/2005 | Bierman |
| 6,951,550 B2 | 10/2005 | Bierman |
| 6,972,003 B2 | 12/2005 | Bierman et al. |
| 6,979,320 B2 | 12/2005 | Bierman |
| 6,981,969 B2 | 1/2006 | Chavez et al. |
| 7,014,627 B2 | 3/2006 | Bierman |
| 7,018,362 B2 | 3/2006 | Bierman et al. |
| 7,070,580 B2 | 7/2006 | Nielsen |
| 7,090,660 B2 | 8/2006 | Roberts et al. |
| 7,115,321 B2 | 10/2006 | Sorens et al. |
| 7,153,291 B2 | 12/2006 | Bierman |
| 7,201,739 B2 | 4/2007 | Walborn |
| 7,214,215 B2 | 5/2007 | Heinzerling et al. |
| 7,223,256 B2 | 5/2007 | Bierman |
| 7,250,880 B2 | 7/2007 | Hurrell et al. |
| 7,354,421 B2 | 4/2008 | Bierman |
| 7,413,561 B2 | 8/2008 | Raulerson et al. |
| 7,491,190 B2 | 2/2009 | Bierman et al. |
| 7,520,870 B2 | 4/2009 | Bierman |
| 7,524,307 B2 | 4/2009 | Davis et al. |
| 7,566,325 B2 | 7/2009 | Lim et al. |
| 7,637,894 B2 * | 12/2009 | Fleischer ............... 604/174 |
| 7,651,479 B2 | 1/2010 | Bierman |
| 7,744,572 B2 | 6/2010 | Bierman |
| 7,776,017 B2 | 8/2010 | Ponzi et al. |
| 7,799,001 B2 | 9/2010 | Bierman |
| 7,887,515 B2 | 2/2011 | Bierman |
| 7,967,792 B2 | 6/2011 | Bierman |
| 7,974,681 B2 | 7/2011 | Wallace et al. |
| 8,100,862 B2 | 1/2012 | Bierman |
| 8,105,290 B2 | 1/2012 | Wright et al. |
| 8,900,196 B2 | 12/2014 | Andino |
| 2001/0011164 A1 | 8/2001 | Bierman |
| 2002/0133121 A1 | 9/2002 | Bierman |
| 2002/0161332 A1 | 10/2002 | Ramey |
| 2002/0165494 A1 | 11/2002 | Bierman et al. |
| 2002/0188255 A1 | 12/2002 | Bierman et al. |
| 2003/0055382 A1 | 3/2003 | Schaeffer |
| 2004/0111067 A1 | 6/2004 | Kirchhofer |
| 2004/0170089 A1 | 9/2004 | Rund |
| 2004/0204685 A1 | 10/2004 | Wright et al. |
| 2004/0240324 A1 | 12/2004 | Isbitsky et al. |
| 2005/0038453 A1 | 2/2005 | Raulerson |
| 2005/0075610 A1 | 4/2005 | Bierman |
| 2005/0107738 A1 | 5/2005 | Slater et al. |
| 2005/0192539 A1 | 9/2005 | Bierman et al. |
| 2005/0215953 A1 | 9/2005 | Rossen |
| 2005/0251157 A1 | 11/2005 | Saadat et al. |
| 2005/0282977 A1 | 12/2005 | Stempel et al. |
| 2006/0025723 A1 * | 2/2006 | Ballarini ............... 604/180 |
| 2006/0052755 A1 | 3/2006 | Lim et al. |
| 2006/0058789 A1 | 3/2006 | Kim et al. |
| 2006/0089600 A1 | 4/2006 | Bierman et al. |
| 2006/0094985 A1 | 5/2006 | Aceti et al. |
| 2006/0135944 A1 | 6/2006 | Bierman |
| 2006/0161087 A1 | 7/2006 | Carter et al. |
| 2006/0184129 A1 | 8/2006 | Bierman |
| 2006/0217669 A1 | 9/2006 | Botha |
| 2006/0247574 A1 | 11/2006 | Maule et al. |
| 2006/0247577 A1 | 11/2006 | Wright |
| 2006/0247661 A1 | 11/2006 | Richards et al. |
| 2006/0270995 A1 | 11/2006 | Bierman |
| 2006/0289011 A1 | 12/2006 | Helsel |
| 2007/0032561 A1 | 2/2007 | Lin et al. |
| 2007/0043385 A1 | 2/2007 | Nobles et al. |
| 2007/0060890 A1 | 3/2007 | Cuppy |
| 2007/0149930 A1 | 6/2007 | Bierman |
| 2007/0173768 A2 | 7/2007 | Bierman |
| 2007/0249980 A1 | 10/2007 | Carrez et al. |
| 2007/0276332 A1 | 11/2007 | Bierman |
| 2007/0276333 A1 | 11/2007 | Bierman |
| 2008/0027392 A1 | 1/2008 | Bierman |
| 2008/0249476 A1 * | 10/2008 | Bierman et al. ............... 604/175 |
| 2009/0043260 A1 | 2/2009 | Bierman |
| 2009/0254040 A1 | 10/2009 | Bierman et al. |
| 2009/0299294 A1 | 12/2009 | Pinkus |
| 2009/0306603 A1 | 12/2009 | Bierman et al. |
| 2010/0179482 A1 | 7/2010 | Wright et al. |
| 2010/0179483 A1 | 7/2010 | Wright et al. |
| 2011/0178467 A1 | 7/2011 | Bierman et al. |
| 2011/0264050 A1 | 10/2011 | Henry et al. |
| 2011/0282291 A1 | 11/2011 | Ciccone |
| 2012/0041378 A1 | 2/2012 | Bierman |
| 2013/0079723 A1 | 3/2013 | Andino et al. |
| 2015/0088076 A1 | 3/2015 | Andino |

FOREIGN PATENT DOCUMENTS

| | | |
|---|---|---|
| DE | 2341297 A1 | 4/1975 |
| EP | 0064284 A2 | 11/1982 |
| EP | 0114677 A2 | 8/1984 |
| EP | 0169704 A1 | 1/1986 |
| EP | 0247590 A2 | 12/1987 |
| EP | 0263789 A1 | 4/1988 |
| EP | 0356683 A1 | 3/1990 |
| EP | 0367549 A2 | 5/1990 |
| EP | 0720836 A2 | 7/1996 |
| EP | 0 931 560 | 7/1999 |
| FR | 2381529 A1 | 9/1978 |
| FR | 2598625 A1 | 11/1987 |
| GB | 2063679 A | 6/1981 |
| GB | 2086466 A | 5/1982 |
| GB | 2178811 A | 2/1987 |
| GB | 2211417 A | 7/1989 |
| GB | 2472268 A | 2/2011 |
| JP | 52-4691 | 2/1977 |
| JP | 62201159 A | 9/1987 |
| JP | 63-501477 | 6/1988 |
| JP | 01308572 A | 12/1989 |
| JP | 1995-28563 | 5/1995 |
| WO | 8001458 A1 | 7/1980 |
| WO | 90/04991 A1 | 5/1990 |
| WO | 9005559 A1 | 5/1990 |
| WO | 9116939 A1 | 11/1991 |
| WO | 9203070 A1 | 3/1992 |
| WO | 9203923 A1 | 3/1992 |
| WO | 9219309 A1 | 11/1992 |
| WO | 9219314 A1 | 11/1992 |
| WO | 9412231 A1 | 6/1994 |
| WO | 9421319 A1 | 9/1994 |
| WO | WO 96/10435 | 4/1996 |
| WO | 9715337 A1 | 5/1997 |
| WO | 9715342 A1 | 5/1997 |
| WO | WO 98/53872 | 12/1998 |
| WO | 9955409 A1 | 11/1999 |
| WO | 2004016309 A2 | 2/2004 |
| WO | 2005105194 A1 | 11/2005 |
| WO | 2007117655 A2 | 10/2007 |
| WO | 2008051810 A2 | 5/2008 |

(56) References Cited

FOREIGN PATENT DOCUMENTS

| WO | 2008151047 A1 | 12/2008 |
|---|---|---|
| WO | 2009055739 A1 | 4/2009 |
| WO | 2010102153 A1 | 9/2010 |

OTHER PUBLICATIONS

ARROW International, Inc. Multiple-Lumen Central Venous Catheterization Product with ARROWgard™ Antiseptic Surface, 6 pgs., K-24703-1008 (Apr. 1994).
ARROW® "Snap-Lock" Catheter/Syringe Adapter, 1 page, K-05500-103A (Jan. 1990).
PCT/US2010/051659 filed Jun. 10, 2010 International Search Report dated Dec. 3, 2010.
PCT/US2010/051706 filed Jun. 10, 2010 International Search Report and Written Opinion dated Dec. 2, 2010.
U.S. Appl. No. 13/498,117, filed Dec. 10, 2012 Final Office Action dated Nov. 2, 2015.
U.S. Appl. No. 13/498,117, filed Dec. 10, 2012 Non-Final Office Action dated Jul. 22, 2015.
U.S. Appl. No. 13/498,118, filed Jul. 2, 2012 Final Office Action dated Oct. 22, 2015.

\* cited by examiner

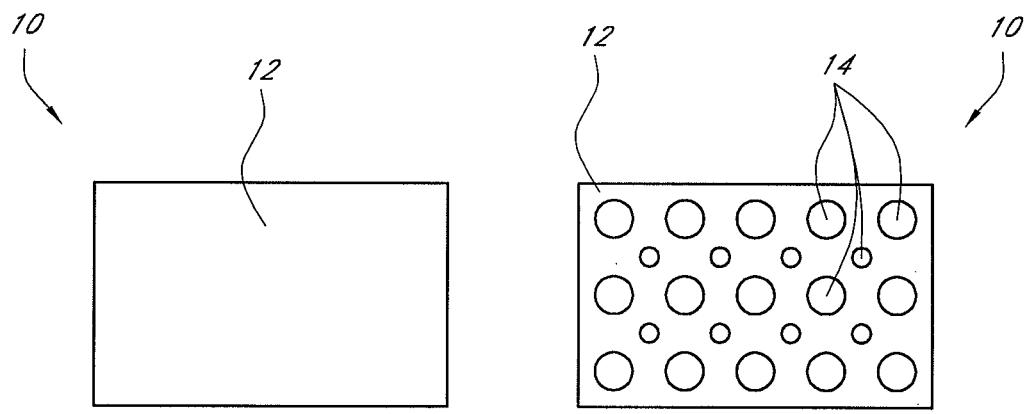
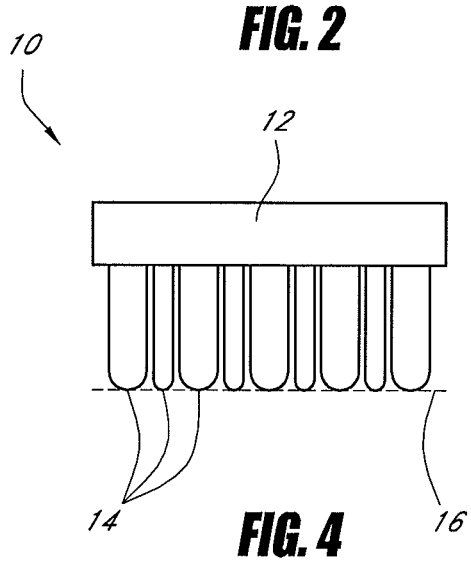
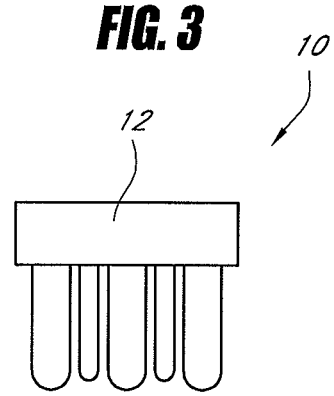
FIG. 2　　FIG. 3　　FIG. 4　　FIG. 5

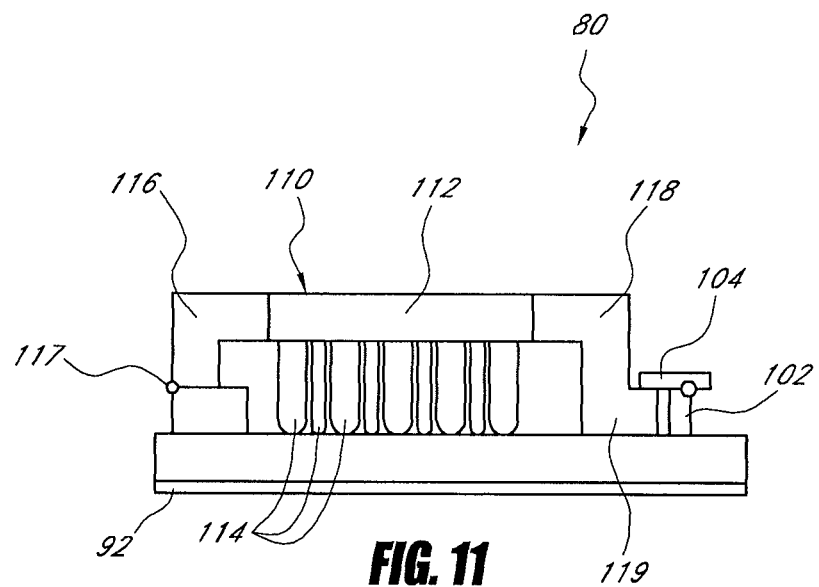
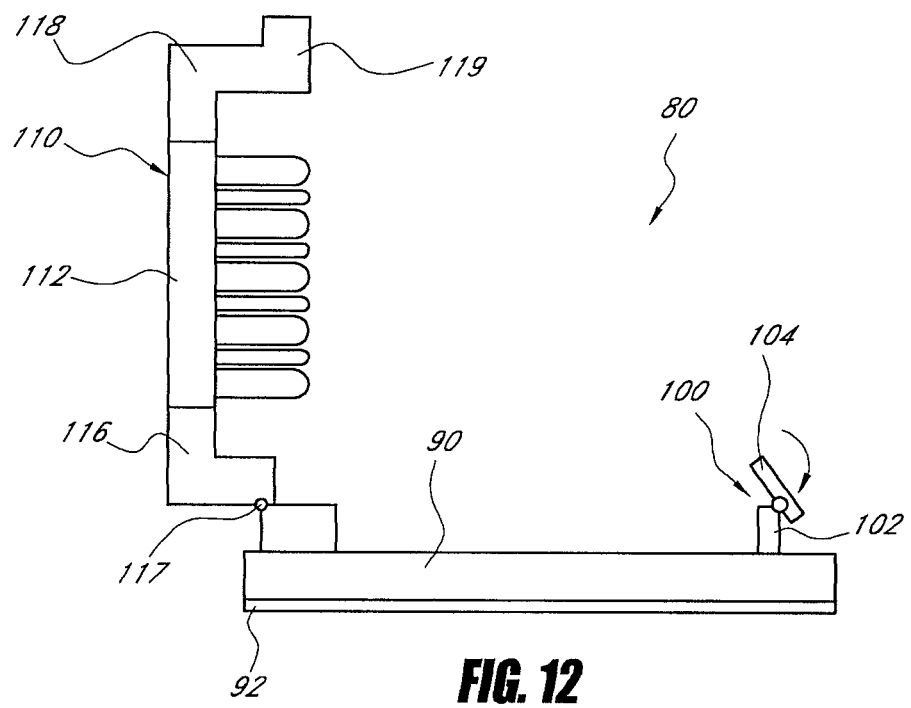

SECUREMENT SYSTEM FOR A MEDICAL ARTICLE

RELATED APPLICATION

This application claims the benefit of U.S. Provisional Application No. 60/950,225, filed on Jul. 17, 2007, entitled "SECUREMENT OF A MEDICAL ARTICLE TO A PATIENT USING A PLIANT HOLDING DEVICE," which is hereby incorporated by reference in its entirety.

BACKGROUND

Field of the Invention

The present invention relates to a system for securing a medical article to a patient.

Description of Related Art

Medical patients are often in need of repetitious administering of fluids or medications, or repetitious draining of fluids. It is very common in the medical industry to utilize medical tubing to provide various liquids or solutions to a patient. For example, short, peripherally-inserted, intra-arteriovenous catheters are used to direct fluids and/or medications directly into the bloodstream of the patient, or withdraw fluids from the patient. Often, it is desirable to maintain such catheterization or medical tube insertion over an extended period of time during the treatment of a patient. In some instances, a medical article may be attached to a patient for a lengthy period of time, requiring minimal movement for proper functioning.

It is often advantageous to restrict the movement of the medical tube or article, particularly when the medical article is to be administered to the patient over an extended period of time. A medical article that is not securely attached to the patient may move around, which may cause discomfort or injury to the patient, restrict the administering of fluids or medications or the draining of fluids, cause infection, or become dislodged from the patient unintentionally.

It is common for medical providers to affix the medical article to the patient and to attempt to restrict movement of the medical article by taping the medical article to the patient's skin. Medical articles commonly attached in this way include medical lines, luer locks or other types of connectors, and wound dressings, which are often taped over a wound to secure the dressing and to provide compression to the wound. Securing a medical article with tape, however, has certain drawbacks.

Tape used to secure a medical article, for example at an insertion site of the medical article on the patient's skin, can collect contaminants and dirt. Such collection of contaminants and dirt can lead to infection. Normal protocol therefore requires periodic tape changes in order to inhibit germ growth. Periodic tape changes may also be necessary when replacing or repositioning the medical article.

Frequent tape changes lead to other problems: excoriation of the patient's skin and adherence of contaminant's to the medical article. Repeated removal of tape can excoriate the skin and cause discomfort to the patient. Additionally, removal of tape can itself cause undesired motion of the catheter device upon the patient and irritation of the patient's skin. Repeated applications of tape over the medical article can lead to the build up of adhesive residue on the outer surface of the medical article. This residue can result in contaminants adhering to the medical article itself, increasing the likelihood of infection.

In addition, valuable time is spent applying and reapplying the tape to secure the medical article. And medical providers often remove their gloves when taping because most find the taping procedure difficult and cumbersome when wearing gloves. Not only does this further lengthen the procedure, but it also may subject the medical provider to possible infection and increase the risk of needle-stick. To add to this, residue buildup on the medical article can make the medical article sticker and more difficult to handle for medical providers.

When tape is used to secure dressings over a wound, periodic changes of the dressing are required, which necessitates removal and reapplication of the tape. As discussed above, the frequent removal and reapplication of adhesive tape to the skin of the patient, which is often performed daily, can excoriate the skin in the area around the dressing. Also, sometimes the tape does not adhere well to the dressing when the dressing absorbs fluids or is saturated with medicine. Without proper adherence, it can be difficult to maintain proper compression on the wound or even keep the dressing in place.

Tape also fails to limit medical article motion and, therefore, contributes to motion related complications like phlebitis, infiltration and catheter migration. Consequently, devices have been proposed to address the problems of using tape.

It is desirable to avoid directly taping a medical article to a patient. There is a need to provide a simple, yet effective device for securely holding a medical article in place on a patient's skin, while avoiding aggravating the site at which the medical article is mounted. With the increased concern over rising health care costs, there is also a need for simple and less expensive alternatives to safely securing medical articles. Therefore, a need exists for an improved medical article securement system for use with a patient that overcomes the problems associated with current options.

SUMMARY

One aspect of the present invention thus involves a device for securing a medical article to a patient. The device includes a body member and a plurality of tentacles extending from the body member. The tentacles are configured to conform to at least a portion of an outer surface of the medical article at least when the device is pressed against the medical article.

Another aspect involves a method of securing a medical article to a patient. The method comprises positioning a medical article relative to a patient and positioning a securement device relative to the medical article. The securement device has a plurality of pliant tentacles. The method further comprises pressing the securement device against the medical article and deforming the tentacles so that the tentacles surround at least a portion of the medical article. The method further includes affixing the securement device to the patient.

Yet another aspect involves a system for securing a medical article to a patient. The system includes an anchor pad that has a lower surface at least partially covered by an adhesive for contacting the patient's skin and a body member supported by the anchor pad. The system further includes a plurality of pliant fingers that extend from the body member and are configured to deform when pressed against the medical article.

Still another aspect involves a securement device that includes a base, a cover, and a receiving area. The cover is moveable with respect to the base between an open position in which at least a portion of the receiving area is exposed and a closed position in which the portion of the receiving area is covered. The device further includes a plurality of tentacles configured to at least initially apply pressure to a secured medical article. At least a portion of the tentacles are compressible when the cover is in the closed position and the secured portion of the medical article is disposed in the receiving area.

Further aspects, features and advantages of the present invention will become apparent from the detailed description of certain embodiments that follows.

BRIEF DESCRIPTION OF THE DRAWINGS

The above mentioned and other features of the invention will now be described with reference to the drawings of several embodiments of the present securement devices and systems. The illustrated embodiments of the securement devices and systems are intended to illustrate, but not to limit the invention. The drawings contain the following figures:

FIG. 2 is a top view of the securement device from FIG. 1.

FIG. 3 is a bottom view of the securement device from FIG. 1 and shows a plurality of tentacles having different diameters.

FIG. 4 is a front view of the securement device of FIG. 1.

FIG. 5 is a side view of the securement device of FIG. 1.

FIG. 11 is a front view of the securement system of FIG. 8, and shows the securement device engaged with the latch in a closed position.

FIG. 12 is another front view of the securement system of FIG. 8, and shows the securement device disengaged from the latch and in an open position.

DETAILED DESCRIPTION OF CERTAIN EMBODIMENTS

Figure 1:
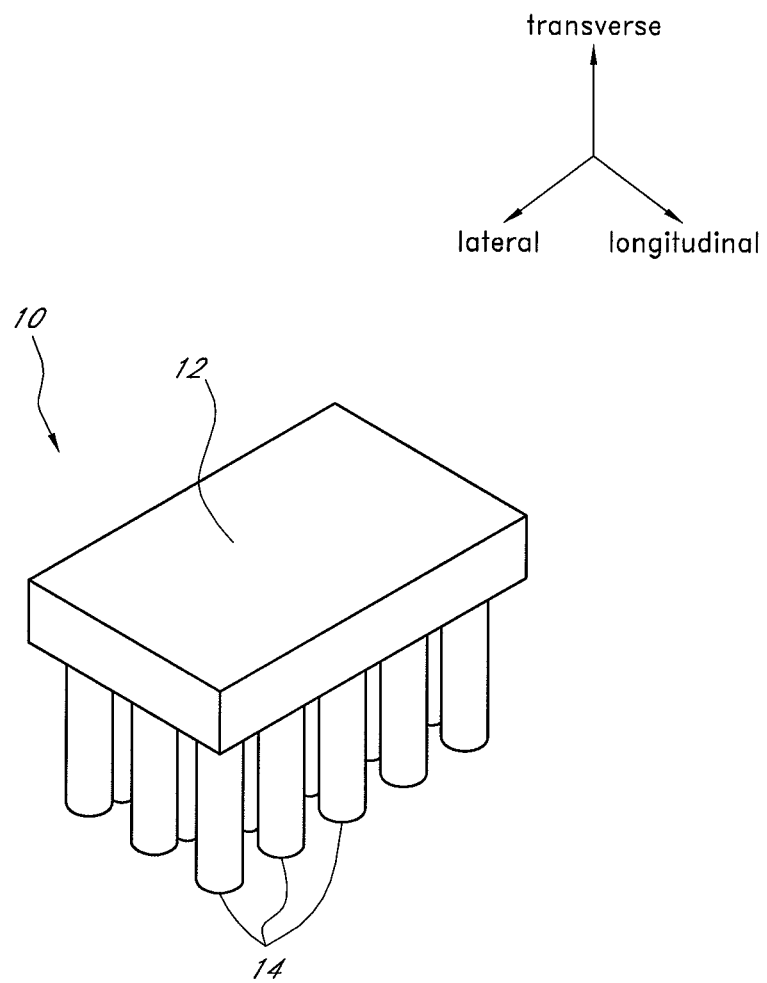
FIG. 1 is a perspective view of a securement device in accordance with an embodiment of the present invention.

The present embodiments of the medical article securement system may be utilized to secure a variety of types of medical articles. In particular, embodiments relate to securement systems, devices, and methods used to fix a medical article such as a catheter device or a wound dressing on the surface of the skin of a patient. In light of the present disclosure, however, it will be understood by one of skill in this art that the securement system and devices disclosed herein can be successfully utilized in connection with many types of medical articles that include fluid drainage and delivery tubes and electrical wires, in addition to a variety of different types of catheters, wound dressings, or other medical articles. For example, but without limitation, the securement device disclosed herein can be configured to receive and secure central venous catheters, peripherally inserted central catheters, hemodialysis catheters, Foley catheters, hubs, catheter adaptors, fluid supply lines, surgical drainage tubes, feeding tubes, chest tubes, nasogastric tubes, dressings, bandages, sutures, medicinal patches, and scopes, as well as electrical wires or cables connected to external or implanted electronic devices or sensors. One skilled in the art can also find additional applications for the devices and systems disclosed herein. Thus, the illustrations and descriptions of the securement system in connection with a medical article are merely exemplary of one possible application of the securement system.

The securement system described herein is especially adapted to arrest lateral and/or transverse movement of a medical article, as well as hold the medical article against the patient. The securement system accomplishes this without meaningfully impairing (i.e., substantially occluding) fluid flow through a medical article such as a catheter. As described below, the securement device to accomplish this includes, among other aspects, pliant tentacles which may compress when pressed against the medical article.

The securement system may further inhibit longitudinal motion of the medical article. For example, one or more tentacles can abut against a generally longitudinally facing surface of the medical article and inhibit longitudinal motion of the secured portion of the medical article. Surface friction between the one or more tentacles and the medical article can inhibit longitudinal motion and/or rotation of the medical article with respect to the securement system.

As will be additionally described below, when the securement device is pressed over a medical article, the tentacles that contact the medical article may compress and bend to accommodate an outer surface of the medical article. The outer surface may have a tubular, conical, or any other shape as explained below. By this, a portion of the medical article may be surrounded and closely held by the tentacles to form a stable mount. Because the medical article may be held on a plurality of sides, movement of the medical article is inhibited.

The securement system releasably engages the medical article. This allows the medical article to be disconnected from the securement system, and from the patient, for any of a variety of known purposes. For instance, the medical provider may want to remove the medical article from the securement system to ease disconnection of two connected medical articles or to clean the patient. The disengagement of the medical article from the securement system, however, can in some embodiments be accomplished without removing the securement system from the patient.

In addition, at least the securement device is not destroyed during disengagement of the securement system. In this way, the securement device can be reused. It is not limited to use for only one medical article, but can be used multiple times for the same medical article or sometimes for different medical articles. The securement system can further be used with multiple medical articles at a single time. For example, two medical lines could be secured by the device. The two lines need not be arranged along the same axis to be secured by the device. After disengagement of the medical article, the securement device is ready for re-engaging with the same or sometimes a different medical article.

The securement system is configured to secure medical articles having a plurality of different shapes and/or sizes. The pliant tentacles may conform to the shape of a portion of the medical article, thereby allowing medical articles of different sizes and shapes to be securely held on the skin of the patient. For example, the securement system may be used to hold a substantially linear medical article such as a drainage tube against the skin of the patient. The securement system may additionally be used to secure a medical article with an elongated body and a laterally extending surface, such as a winged catheter, or other medical articles that are not substantially linear, for example. In some embodiments, the tentacles of the securement system are made of a resilient material that will substantially return to its original shape, thereby allowing the securement system to be used repeatedly with the same or a different medical article. A detailed description of embodiments of a securement system, and its associated method of use, now follows.

With reference now to FIG. 1, an embodiment of a securement device 10 includes a body member 12 and a plurality of tentacles 14. The tentacles 14 protrude from, or extend from, the body member 12. The securement device 10 is configured to be placed over a medical article and secure the medical article to the patient, as described below in reference to FIGS. 6 and 7.

To assist in the description of the components of embodiments of the anchoring system, the following coordinate terms are used, consistent with the coordinate axes illustrated in FIG. 1. A "longitudinal axis" is generally parallel to a section of a medical article retained by the securement device 10. In FIG. 1, the longitudinal axis is generally parallel to the shorter sides of the body member 12. A "lateral axis" is normal to the longitudinal axis and is generally parallel to the plane of the body member 12. In FIG. 1, the lateral axis is generally parallel to the longer sides of the body member 12. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The terms "proximal" and "distal" are used in reference to the center of the patient's body.

As can be seen in a top view of the securement device 10 in FIG. 2, the body member 12 is illustrated as being substantially rectangular. The body member 12 may, however, be formed in other shapes. For example, the body member 12 may be substantially square, circular, or have a "dog bone" like shape. Any number of factors may be considered when selecting a shape of the body member 12, including the desired application of the securement device 10, manufacturing considerations, and shape of the portion of the medical article to be retained.

Figure 6:
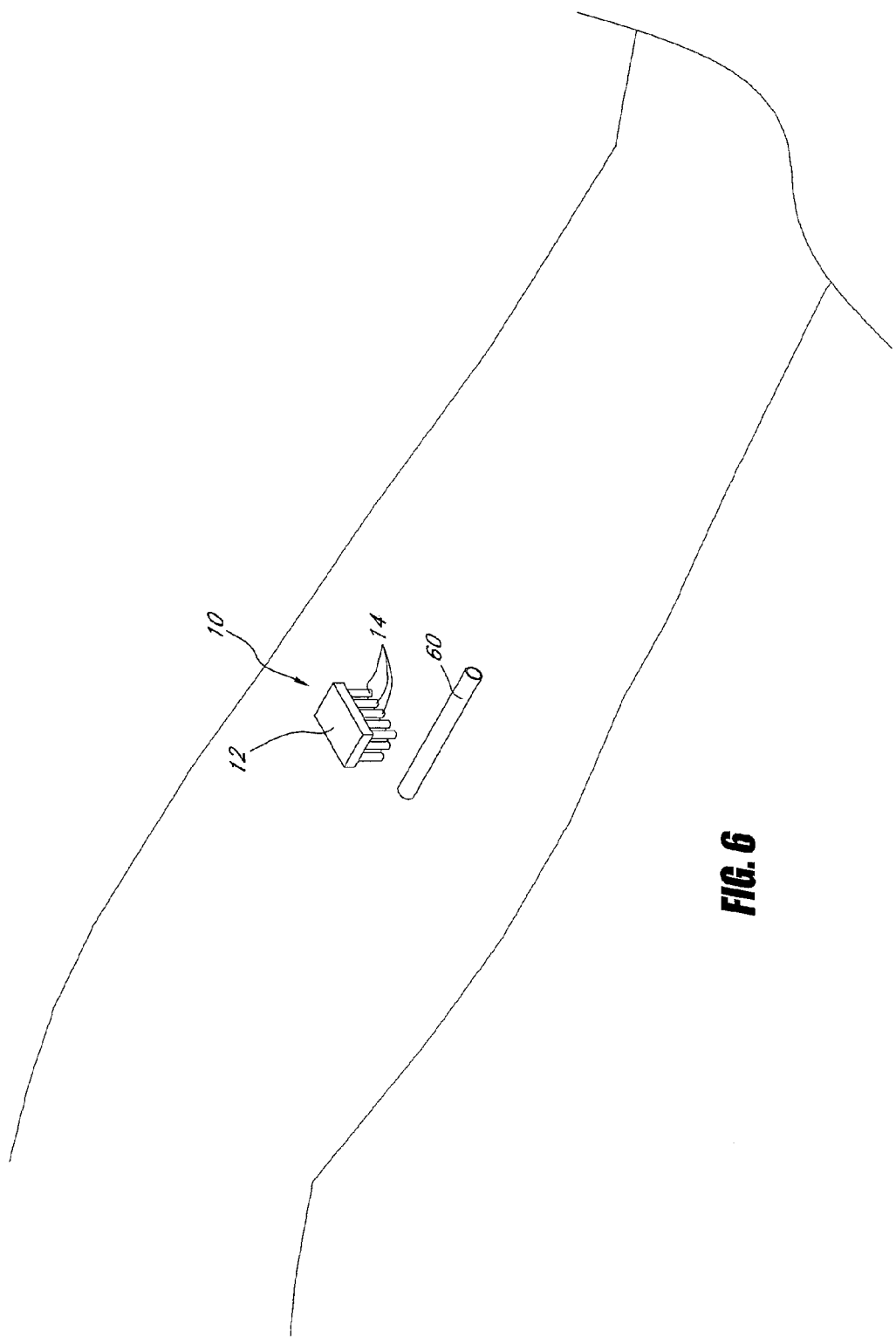
FIG. 6 is a perspective view of the securement device of FIG. 1 positioned above a medical article placed on a patient's skin.

As can be seen in a front and side view of the securement device 10 in FIGS. 4 and 5, respectively, the body member 12 is illustrated as being substantially planar. Such planar configuration may increase the ease with which tape or a strap can be placed over the top of the body member 12 to attach the securement device 10 to a patient, as illustrated in FIG. 6. Nonetheless, the body member 12 is not limited to being planar. For example, the top of the body member 12 may have a rounded shape or a protrusion forming finger grips on either side. The body member 12 may include a sloping surface or a plurality of surfaces arranged in a stepped fashion.

The body member 12 may be manufactured from one or more of a variety of materials. The materials used may be selected from any materials commonly used for medical devices, including materials with anti-microbial properties and/or materials that are latex-free. Suitable materials include, without limitation, plastics, polymers, gels, silicone, polyurethane, natural rubber, and synthetic rubber.

Depending on the size, shape, and materials from which the body member 12 is constructed, the body member 12 can be relatively stiff or flexible. In certain embodiments, the body member 12 is configured to flex to accommodate the surface on which it is mounted, such as a curved surface of the patient's skin. The degree of stiffness or flexure can vary based on the intended use of the device.

The tentacles 14 are formed as elongated, flexible protrusions. The tentacles 14 are shaped with a thickness and formed of a material that allows each tentacle to be resilient, compressible, and have at least a limited degree of elasticity. Thus, the tentacles 14 may substantially maintain their shape in the absence of pressure, but deform when a force is applied.

The tentacles 14 are arranged across at least a portion of one surface of the body member 12 to form a receiving surface 16 that is compressible. The receiving surface 16 may or may not be substantially planar. When the securement device 10 is mounted over a medical article, the tentacles 14 will compress, thereby at least partially conforming to a portion of the medical article. The body member 12 may have tentacles 14 on more than one side. For example, a tentacle 14 covered bottom surface and the patient's skin could receive a first medical article therebetween. A tentacle 14 covered top surface and tape, a strap, and/or a cover member could receive a second medical article therebetween.

Any number and arrangement of the tentacles 14 can be used. As can be seen in the a bottom view of the securement device 10 in FIG. 4, the tentacles 14 are illustrated as being uniformly arranged in an array defined by a plurality of rows and columns. Of course, the tentacles 14 may be arranged in a different pattern or randomly. The tentacles 14 are illustrated as being arranged in a closely spaced pattern. Such closely spaced pattern provides a secure holding structure for a medical article.

To increase how closely the tentacles 14 may be arranged, the illustrated tentacles 14 are provided in different widths or diameters. Of course, the tentacles 14 can also be provided in substantially similar widths or diameters. The width or plurality of widths of the tentacles 14 can be selected to provide different degrees of pliancy to accommodate different types of medical articles. For example, tentacles of a smaller width may be provided to secure wires, while tentacles of a larger width may be provided to secure a catheter hub. In some embodiments, the tentacles in one area may be substantially wider than the tentacles in another area such that different areas of a single securement device 10 can be used to secure different types of medical articles. In other embodiments, the tentacles 14 have diameters of close to 1 nanometer and are formed from single-walled or multi-walled carbon nanotubes (CNTs).

As can also be seen in the bottom view of the securement device 10, the tentacles 14 are illustrated as having a circular cross section. A circular cross section may facilitate bending in any direction. Of course, one or more of the tentacles 14 may be formed as other shapes. For example, half of the tentacles could be round, while the other half could have semicircular depressions on four sides, thereby being complementary to the round tentacles and allowing all of the tentacles to be formed such that the space between tentacles is minimized. The tentacles may also have a square or rectangular cross section. A portion of a tentacle 14 can have a cross-section that is different from a cross-section of another portion of the same tentacle 14. Thus, a tentacle 14 can have a lower circular cross-section and an upper square cross-section or vice versa.

As can be seen in a front and side view of the securement device 10 in FIGS. 4 and 5, respectively, the tentacles 14 are illustrated as extending from the body member 12 in a substantially normal direction and have substantially the same length. The tentacles 14 may, however, be configured to extend in a direction other than normal to the body member 12, and the tentacles 14 may be angled with respect to any of a longitudinal, lateral, and transverse direction. One or more of the tentacles 14 may have varying lengths, thereby forming a non-planar receiving surface 16.

The tentacles 14 may be manufactured from one or more of a variety of materials. The material used for the tentacles 14 desirably has an inherent resilience. The tentacles 14 may be formed of plastics, polymers, gels, silicone, polyurethane, natural rubber or synthetic rubber, for example. Other useable materials include materials suitable for medical use, such as medical materials that exhibit resilience.

The tentacles 14 may additionally be manufactured from or coated with a material that has a high frictional coefficient with one or more medical articles. For example, a portion of one or more of the tentacles 14 may comprise an adhesive suitable for attachment to a medical article. In addition, one or more of the tips of the tentacles 14 may include a tacky substance, thereby forming a receiving surface 16 or portion thereof that is configured to attach to the medical article and/or the patient's skin. When the medical article is brought into contact with the adhesive or tacky substance, movement of the medical article in relation to the tentacles 14 will be inhibited. Adhesive and tacky surfaces of the securement device 10 may be covered with a release liner paper before application of the securement device 10.

A phase change material may be included in the securement device 10. For example, some or all of the tentacles 14 may comprise a material that changes from a substantially hard or rigid phase to a semi-hard or malleable phase in response to applied pressure. In such an embodiment, the tentacles 14 containing the phase change material could mold around the surface of a medical article when pressed against the medical article.

A phase change material can be included in the tentacles 14 or between the tentacles 14. For example, a phase change material disposed between some or all of the tentacles 14 may be responsive to an increase in heat caused by placing the securement device 10 in close proximity to the skin of a patient. In such situation, the material may change from a hard phase to a malleable phase and receive a portion of a medical article, as well as accommodate tentacles which may have been compressed or deformed by the introduction of the medical article.

A phase change material may also harden over time. For example, all or portions of the securement device 10 may be composed of a hardening phase change material that may be supplied to a medical provider in a sealed bag or container and that may harden when exposed to the humidity outside of the bag or container. Thus, when the securement device 10 is removed from the container and applied to a medical article and/or a patient, all or a portion of the medical article 10 may harden into a shape complementary to the medical article and/or patient.

One example of a phase change material is a thermally-conductive phase change material, which may be obtained commercially from several vendors. Such phase change material may consist of a wax (high molecular weight hydrocarbon, filled with thermally conductive solid particles such as BN, alumina, diamond, silver flake, carbon nanofibrils, etc. Typically solid at room temperatures, the phase change material may soften or melt at elevated temperatures, for example as caused by being in close proximity to a patient's skin. The phase change material may be covered by a release liner paper that can be peeled away before application of the securement device 10.

Other phase change materials may be responsive to pressure and/or humidity. The phase change material may transform from a hard phase into a softer phase, and in some cases may become molten at operating temperatures. The phase change material may also harden or solidify, thereby changing from a soft or gel phase into a more solid or rigid phase. Phase changes may or may not be permanent.

The body member 12 and the tentacles 14 can be formed as an integral unit, by molding or co-molding for example, using the same or different materials. Alternatively, the tentacles 14 can be permanently attached to the body member 12, for example by sonic welding, again using the same or different materials. Selecting the body member 12 and the tentacles 14 to be different materials allows different degrees of stiffness in the body member 12 and the tentacles 14. In the illustrated embodiments, the tentacles 14 are unsegmented, but of course the tentacles 14 could be formed from segments.

Figure 7:
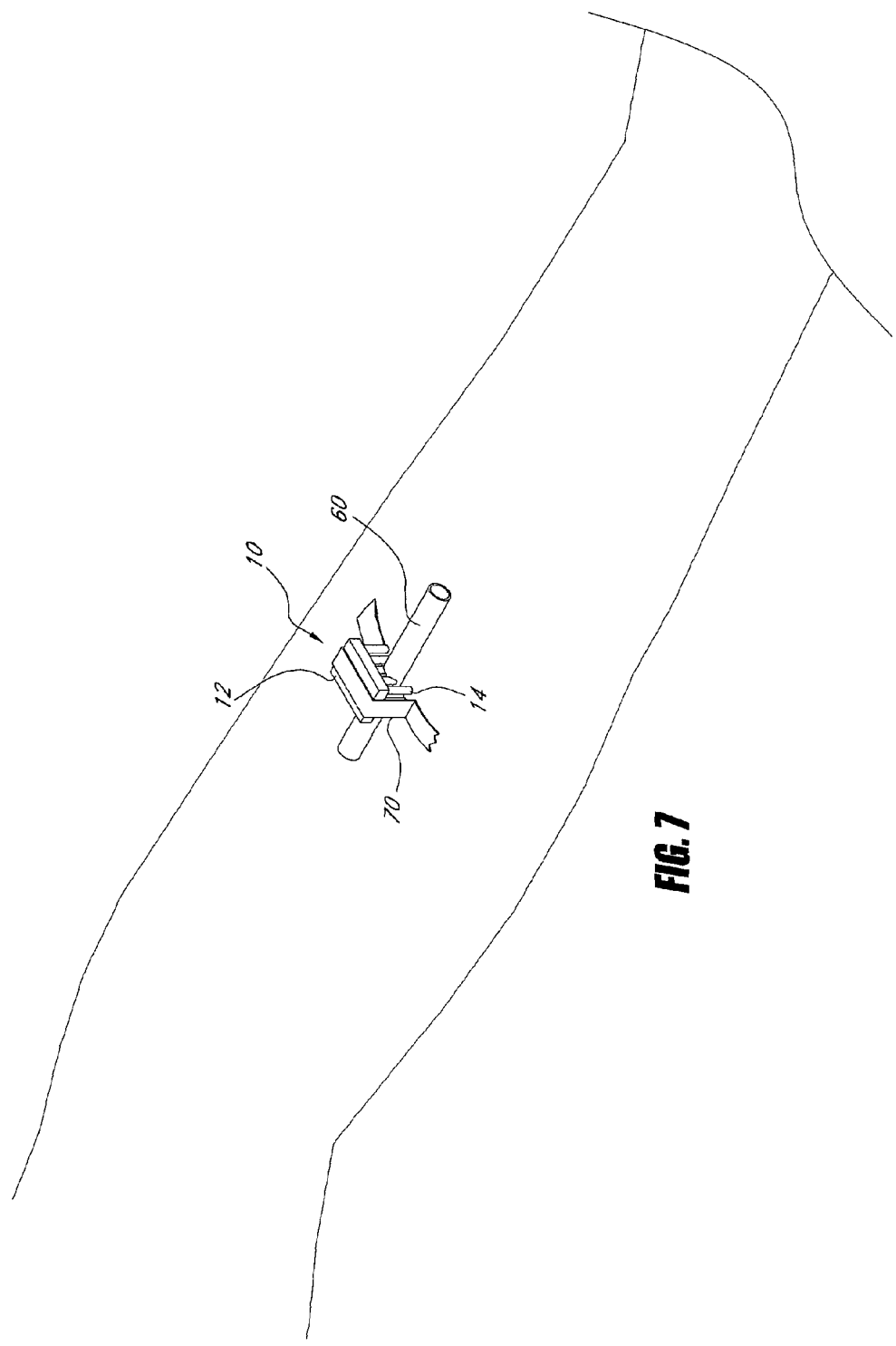
FIG. 7 is a perspective view of the securement device of FIG. 1 secured over the medical article.

A medical article 60 can be secured to a patient by the securement device 10, as shown in FIGS. 6 and 7. The medical article 60 can be initially placed on a patient, such as against the skin of the patient. After placing the securement device 10 above the medical article 60, as shown in FIG. 6, a medical provider can then lower the securement device 10 over the medial article 60. Alternatively, the medical article 60 is placed in contact with the securement device 10 prior to the medical article being placed against the patient's skin.

In embodiments of the securement device 10 in which an adhesive capable of attaching to the patient is disposed on some or all of the tentacles 14, the medical provider may attach the medical article 60 to the patient by lowering the securement device 10 over the medical article 60 and pressing the securement device 10 onto the patient. These actions will cause at least some of the tentacles 14 to conform to a portion of the medical article 60, while simultaneously adhering the securement device 10 to the patient. Thus, movement if the medical article 60 will be inhibited.

After the securement device has been lowered over the medical article 60, regardless of whether the securement device 10 comprises an adhesive capable of attaching to the patient, the medical provider can attach the securement device 10 to the patient using a length of an adhesive tape 70, such as medical tape, as shown in FIG. 7. The adhesive tape 70 is placed over at least a portion of the top of the securement device 10 and extends from the securement device 10 to attach to the patient. As described above, however, the securement device 10 may be attached to the patient in the absence of the medical tape 70 in some embodiments.

Attaching the medical article 60 to the patient using the adhesive tape 70 in this way not only arrests movement of the medical article 60, but also separates the adhesive tape 70 from an area in which the medical article 60 is located. Thus, any contaminants that gather on or around the adhesive tape 70 will be kept at a distance from the medial article 60 and, in the case that the medical article 60 is a catheter, at a distance from a site at which the medical article 60 is inserted.

Although the securement device 10 is illustrated as being attached to the patient with the adhesive tape 70, any means of fixing the securement device 10 to the patient may be used. Other means of fixing the securement device 10 to the patient include one or more supports, straps, adhesives, and/or anchor pads.

The adhesive tape 70, as illustrated, is a conventional means of attachment and may be secured over the body 12. It is also possible to provide the securement device 10 with a length of tape pre-attached to the body 12. Adhesive portions of the tape would extend from one or more sides of the body 12 and could be covered by a liner, as is known by those skilled in the art, which would be removed by the medical care provider to fix the securement device 14 in place.

As can be seen in FIG. 7, certain ones of the tentacles 14 compress when the securement device 10 is lowered over the medical article 60. These compressed tentacles apply transverse pressure to the medical article 60, thereby holding the medical article 60 against the skin of the patient or against another surface. In addition, certain ones of the tentacles 14 may apply lateral and/or longitudinal pressure to the medical article 60. Such tentacles may surround a portion of the medical article 60 when the securement device 10 is placed over the medical article 60.

Elasticity of the tentacles 14 may provide a cushioning effect so that if the medical article 60 is pulled or moved, the tentacles 14 can cushion any inadvertent motion of the medical article. When the securement device 10 is removed, the tentacles 14 may return to their original elongated shape. Of course, it is also possible for the tentacles 14 to be formed from a material that permanently deforms to accommodate the medical article 60.

To remove or reposition the medical article 60, the medical provider may disconnect one or both sides of the adhesive tape 70 from the patient. The medical article 60 can then be easily manipulated or replaced. The securement device 10 can then be lowered over the medical article 60 again or lowered over another medical article. The other medical article may be similar to the medical 60, or sized or shaped differently. In some embodiments, the tentacles 14 substantially return to their original shape after the medical article 60 is removed.

Although a single medical article 60 is illustrated in FIGS. 6 and 7, one of skill in the art will appreciate that the securement device 10 can be used to secure a plurality of medical devices simultaneously. For example, several medical articles or wires placed together can be accommodated by compression of the tentacles 14. Alternatively, several medical articles separated by a distance less than the width of the securement device 10 can each be secured and their separation maintained. Although the medical article 60 is illustrated as passing under the securement device 10 such that the medical article 60 is substantially parallel to the shorter width of the securement device 10, the medical article 60 may pass under the securement device 10 in any direction.

In the case that the medical article is a wound dressing, the securement device 10 provides compression to at least a portion of the dressing. In some embodiments, the securement device 10 provides compression to the entire surface of the dressing. The securement device 10 may also cushion the wound and provide a protective covering over the wound. Additionally, since the tentacles 14 form a porous receiving surface 16, rather than a solid receiving surface, air can circulate and moisture can evaporate, which promotes healing and reduces the risk of infection. Further, since the tentacles 14 can be made of anti-microbial material, the risk of contaminating the medical article, especially if it is a wound dressing, is greatly diminished. Moreover, the securement device 10 will not adhere to the medical article and thus will not leave residue or pose problems if the dressing, for example, is moist or slippery.

Figure 8:
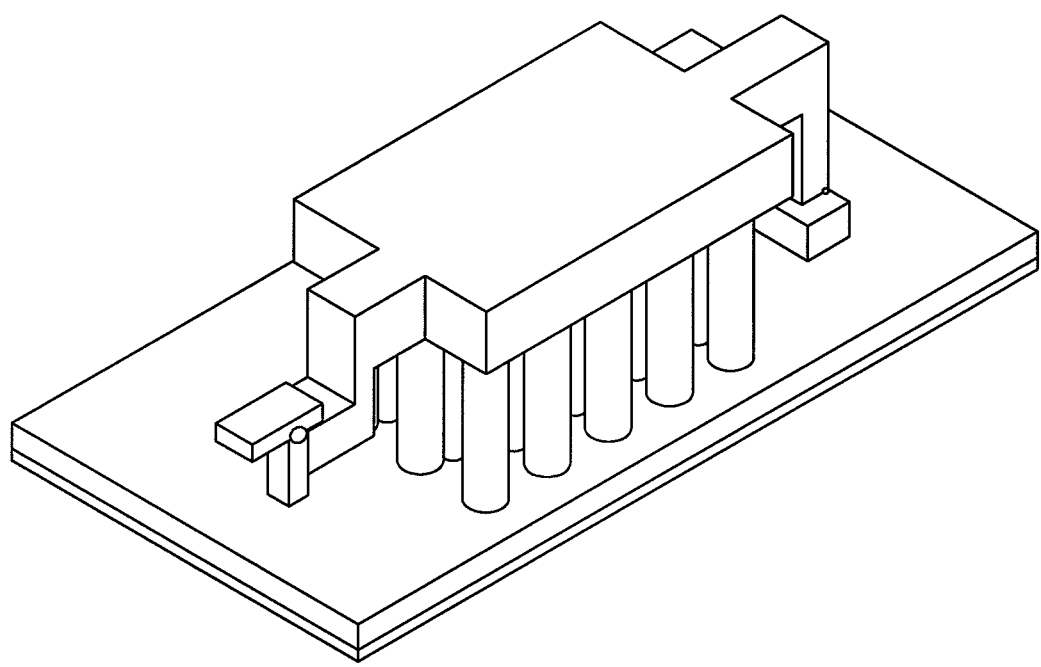
FIG. 8 is a perspective view of a securement system in accordance with another embodiment of the present invention, and shows a securement device, a base, and a latch.

With reference now to FIG. 8, an embodiment of a securement system 80 includes a base 90, a latch 100, and a securement device 110. The latch 100 and the securement device 110 are attached to the base 90. The securement device 110 moves between an open position and a closed position relative to the base 90. The latch 100 secures the securement device 110 to the base 90. The securement system 80 is configured to be placed about a medical article and secure the medical article to the patient, as described below in reference to FIGS. 15 through 17.

Figure 9:
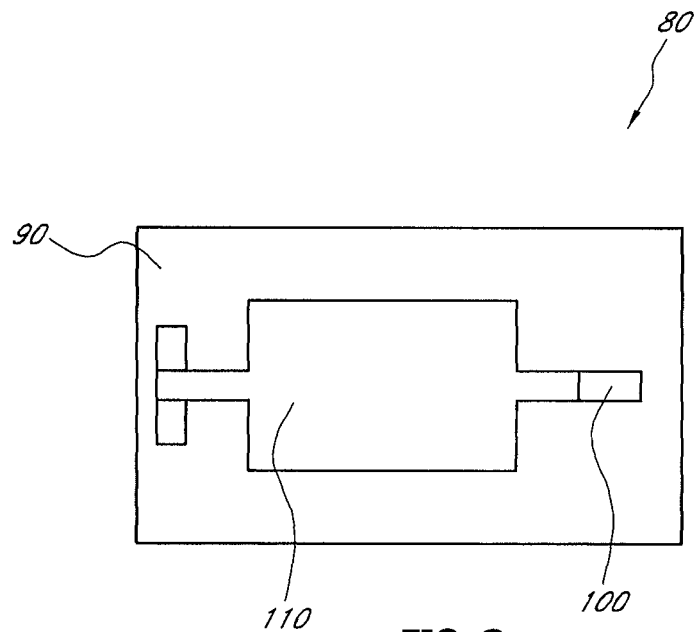
FIG. 9 is a top view of the securement system of FIG. 8.
Figure 10:
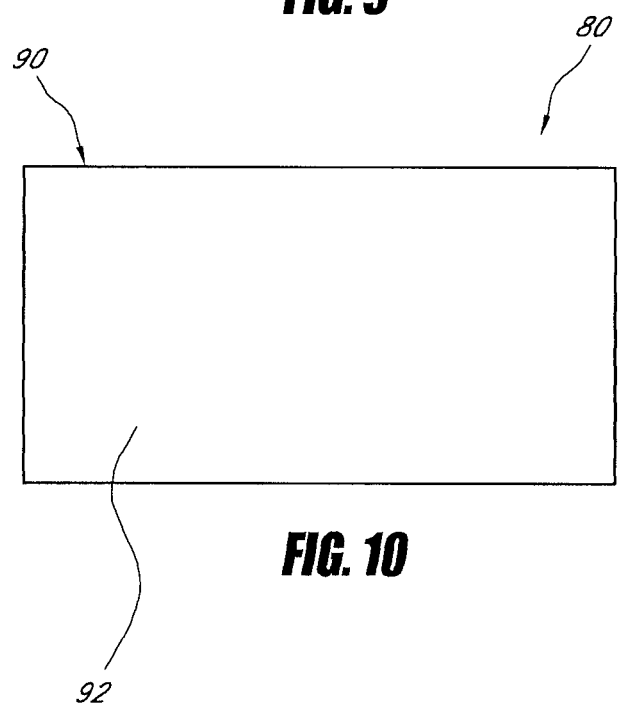
FIG. 10 is a bottom view of the securement system of FIG. 8.

The base 90 is configured to support the securement device 110. At least a portion of the base 90 is configured to receive a portion of a medical article. As can be seen in a top and bottom view of the securement system 80 in FIGS. 9 and 10, respectively, the base 90 is illustrated as having a substantially rectangular shape. As can be seen in a front view of the securement system 80 in FIGS. 11 and 12, the base 90 is illustrated as being a planar member. Of course, the base 90 may have other shapes and sizes. The base 90 may further include a groove or channel. A cross-section of the groove or channel may be substantially the same or vary along the longitudinal axis. For example, the groove or channel may be configured to generally match an outer surface of the secured portion of the medical article.

The longitudinal dimension of the base 90 is preferably sufficiently long to provide stability to the secured portion of the medical article. That is, the longitudinal length of the portion of the medical article placed on the base 90 is sufficient to inhibit rocking of the medical article relative to the base 90 (i.e., to prevent the base 90 from acting as a fulcrum for the medical article).

The lateral dimension of the base 90 is sufficiently long to accommodate the width of the securement device 110, as well as the latch 100. The shape and dimensions of the base 90 may otherwise be varied.

In the illustrated embodiment, a lower surface of the base 90 is configured to be supported by the surface of a patient's skin. An adhesive layer 92 is provided on at least a portion of the lower surface of the base 90 for adhering to the patient. The adhesive layer 92 may comprise a non-allergenic, medical grade adhesive. The adhesive can be either diaphoretic or nondiaphoretic, depending upon the particular application. Of course, any suitable adhesive can be used that is known for medical applications, such as a pressure sensitive adhesive. It is possible to provide the adhesive during manufacture of the system or to attach it during use, for example by means of double stick tape.

As is known to those skilled in the art, a liner (not shown) can be removably secured to the adhesive layer 92 prior to connection to the patient. Any suitable material can be used for the liner, such as a silicone coated polyester film. Other suitable materials include films such as high density polyethylene, polypropylene, polyolefin, or silicon coated paper.

Figure 25:
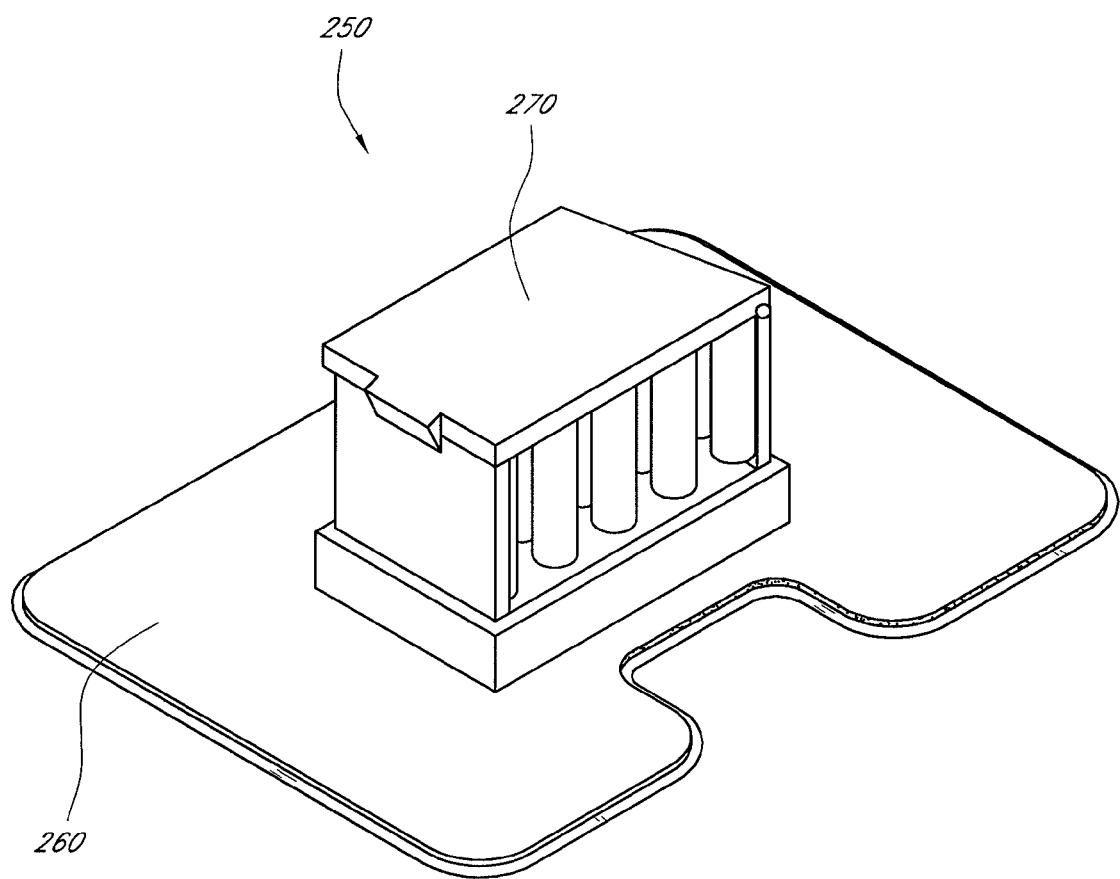
FIG. 25 is a perspective view of a securement system in accordance with another embodiment of the present invention, and shows an anchor pad and a securement device.

Other means to attach the base 90 to the patient may instead or additionally be used. For example, a medical provider can attach tape to the patient and place the tape over a portion of the base 90 or the securement system 80. Alternatively, the base 90 may be provided on an anchor pad, as is illustrated in FIG. 25. Although not illustrated, it will be understood that the base 90 can include suture holes in addition to or instead of the adhesive layer 92 to secure the base 90 to the patient's skin.

The base 90 may be made of a relatively stiff material, such as medically compatible plastics, polymers, or composites. The base 90 can be latex-free. In the alternative, the base 90 may flex to accommodate the surface on which it is mounted or have a curved lower surface. Other materials from which to form the base 90 will be apparent to those skilled in the art.

The latch 100 is attached to the base 90 and is configured to engage the securement device 110. The latch 100 may be placed on any side of the base 90. In the illustrated embodiment, the latch 100 is placed on the side opposite the hinge 117.

As can be seen in a front view of the securement system 80 in FIG. 11, the latch is illustrated as including a post 102, and a retaining member 104 attached by a hinge to the post 102. To engage the securement device 110, a medical provider may depress the outside portion of the retaining member 104 to raise the opposing portion of the retaining member 104, as is shown in FIG. 12. Thereafter, a portion of the securement device 110 may be captured beneath the latch 100.

The latch 100 may be configured in any way that engages the securement device 110 and fastens the securement device 110 over a medical article. In some embodiments, the latch may include a spring or tension device that biases the latch into a closed position. In some embodiments, the latch 100 may be omitted and the securement device 110 fastened over the medical article using other means. For example, the securement device 110 may engage directly with the base 90, or the securement device 110 may be fastened by an adhesive or tape. The latch 100 need not be mechanical and instead, for example, can employ a snap, hook and loop fastener, strap, clasp, adhesive, or other structure known to one having skill in the art.

As can be seen in the front view of the securement system 80, the securement device 110 includes a body member 112, a plurality of tentacles 114, a hinged member 116, and a connection member 118. The hinged member 116 is attached to the base 90. The connection member 118 can engage and be secured by the latch 100. The body member 112 is connected to the hinged member 116 and the connection member 118. The tentacles 114 protrude from, or extend from, the body member 112. The body member 112 and the tentacles 114 may be configured similar to the body member 12 and the tentacles 14 described above in reference to the securement device 10.

The hinged member 116 extends from the base 90 to the body member 112 and elevates the body member 112 such that the tentacles 114 can extend downward from the body member 112. The hinged member 116 thus forms a support for the body member 112. The hinged member 116 is made of a relatively stiff material, such as medically compatible plastics, polymers, or composites. Other materials from which to form the hinged member 116 will be apparent to those skilled in the art.

The hinged member 116 includes a hinged section 117 configured to allow the hinged member 116 to move between at least an open position, which is illustrated in FIG. 12 and enables a medical article to be placed beneath the tentacles 114, and a closed position, which is illustrated in FIG. 11 and presses the tentacles down on top of a medical article (not shown in FIG. 11).

Any type of hinge can be used to implement the hinged section 117. The hinged section 117 may be integral, or may be formed of separate components. An example of an integral hinge for use in the hinged section 117 is a living hinge formed as a buckle of connecting material between the portion of the hinged member 116 that contacts the base 90 and the remainder of the hinged member 116. This living hinge has the advantages of being inexpensive and durable. In an embodiment where the hinged section 117 is formed as a living hinge, the hinged member 116 can be formed as an integral unit, by molding for example.

If desired, a separate hinge element could be used to implement the hinged section 117, as illustrated in FIGS. 11 and 12. A separate hinge may include a spring or may be formed as a leaf spring, for example, to bias the hinged member 116 into certain positions through its pivot swing. For example, a separate hinge may be designed to snap the hinged member 116 into open and closed positions. This holds the securement device 110 in the desired position without assistance from the medical provider, who will likely be attending to the medical article.

In the illustrated embodiment, the hinged member 116 has a generally L-shaped configuration. The hinged member 116 may, of course, be shaped in another configuration that extends between the body member 112 and the base 90. For example, the hinged member 116 may be substantially linear, extending from the base 90 directly to the body member 112.

The connection member 118 extends from the body member 112 such that at least a portion can engage with the latch 100 when the securement device 110 is placed in the closed position. The connection member 116 includes an interlock section 119 configured to engage with the latch 100. In the illustrated embodiment, the interlock section 119 is a protrusion configured to be captured below the latch 100, as shown in FIG. 11. When the latch 100 is depressed, the connection member 116 can disengage from the latch 100, allowing the securement device 110 to move to the open position, as shown in FIG. 12.

Other configurations of the interlock section 119 are possible. For example, the interlock section 119 may include a recess that accepts a corresponding protrusion on the latch 100 or the base 90. In some embodiments, the connection member 118 snaps over or onto a corresponding structure on the latch 100 or the base 90. In still other embodiments, the latch 100 may be omitted when the connection member 118 is configured to directly engage with the base 90 or another structure, such as when a protrusion on the connection member 118 is configured to extend into and engage with the base 90.

The connection member 118 may otherwise be configured similar to the hinged member 116. For example, the connection member 118 may be made of similar materials and/or shaped similar to the hinged member 116.

In some embodiments, the connection member 118 is omitted from the securement system 80. In these embodiments, the securement device 110 may be fastened over a medical article using other means, such as a hinged member configured to snap into a closed position or a support member biased towards the patient's skin. Other means for fastening the securement device 110 over a medical article in the absence of the connection member 118 include an adhesive tape or any other means described above in reference to attaching the securement device 10 to the patient.

Figure 13:
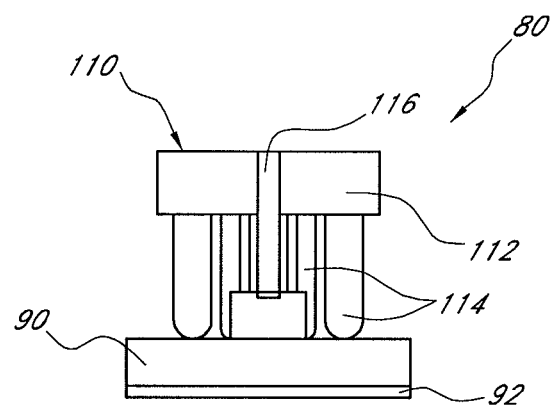
FIG. 13 is a side view of the securement system of FIG. 8 showing the hinge mechanism.
Figure 14:
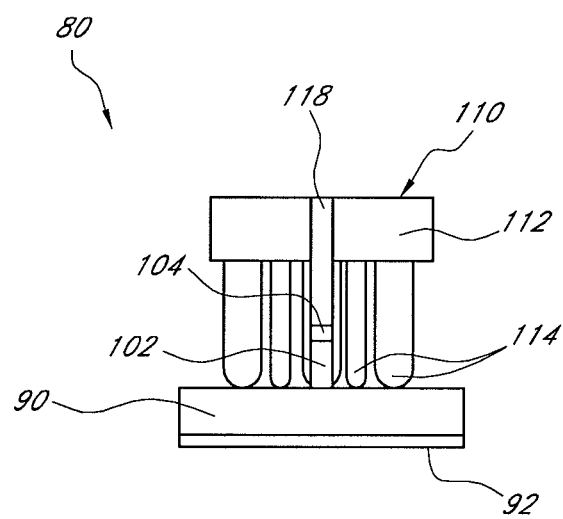
FIG. 14 is a side view of the securement system of FIG. 8 showing the latch mechanism.

As can be seen in side views of the securement device 80 in FIGS. 13 and 14, the hinged member 116 and the connection member 118 are illustrated as being transversely aligned with the body member 112. The hinged member 116 and the connection member 118 may be affixed to the body member 112 by adhesive or ultrasonic welding, for example. It is also possible to form one or both of the hinged member 116 and the connection member 118 as integral with the body member 112, for example by molding.

The hinged member 116 and the connection member 118 may, however, be configured to connect to the body member 112 any number of other ways. For example, the hinged member 116 and/or the connection member 118 may be connected to the top of the body member 112. In such embodiment, the hinged member 116 and/or the connection member 118 can have a fastener, such as a tongue and groove type joint, to connect to the body 46, or may be attached by welding or adhesive, as described above. The body member 112 may be detachably fastened to the hinged member 116 such that the body member 112 can be unfastened and a different body member thereafter fastened to the hinged member 116. In some embodiments, the hinged member 116 and the connection member 118 are integrally formed and may be attached to the top of the body member 112.

In some embodiments, the base 90 is omitted from the securement system 80. In these embodiments, the hinged member 116 can be attached directly to the patient's skin, or to another structure such as an anchor pad. The latch 100 can also be attached to another structure, such as an anchor pad, in these embodiments, or the latch 100 can also be omitted from the securement system 80.

Those of skill in the art will understand that the securement system 80 may be constructed as a single piece or from a plurality of different pieces. For example, the securement device 110 may be formed by injection molding; or the body member 112, the hinged member 116, and the connection member 118 may each be formed separately and thereafter joined together. In one embodiment, the base 90, the latch 100, and/or the securement device 110 is formed by injection molding using a polyethylene or a polypropylene material or nylon. However, other materials can be utilized.

Figure 15:
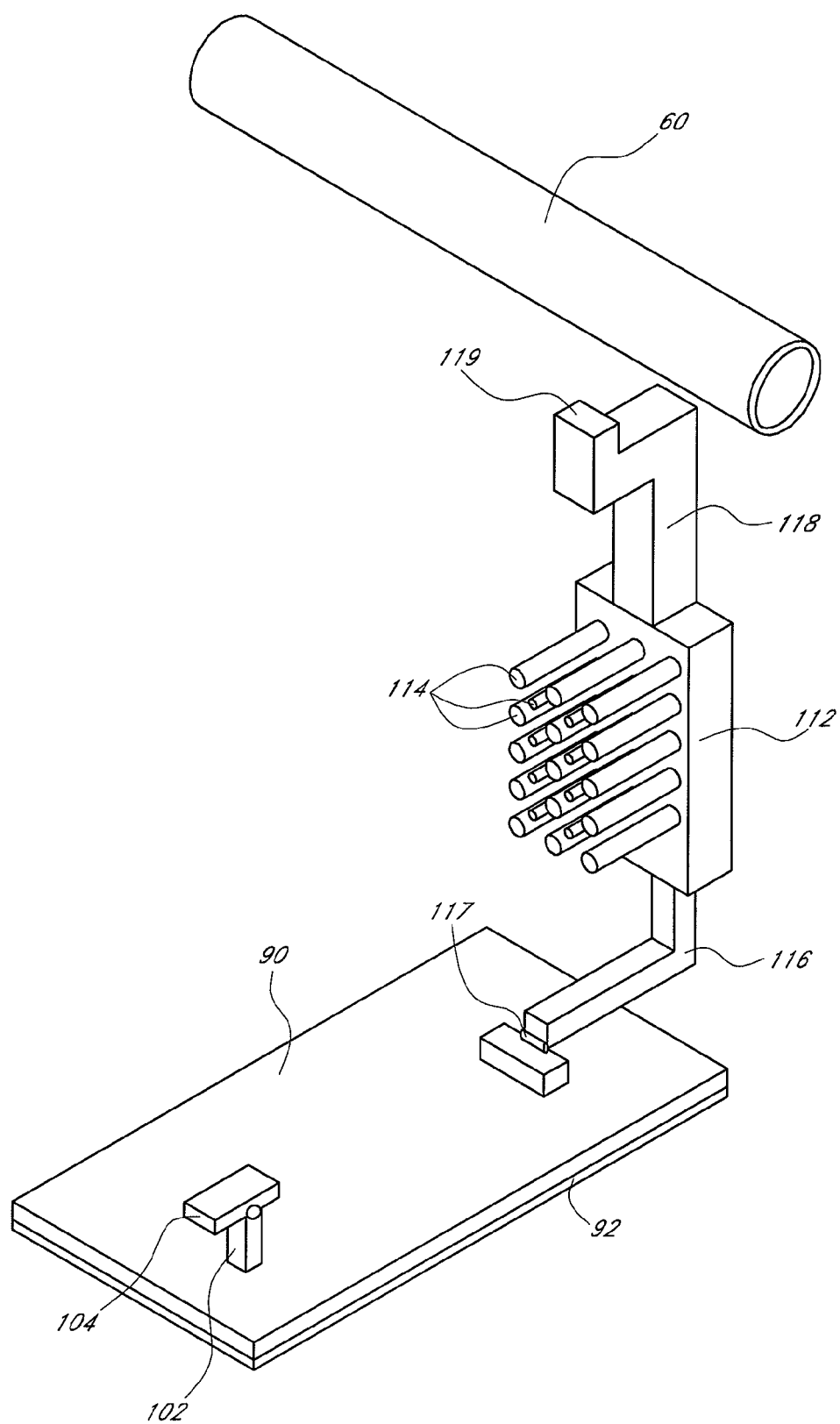
FIG. 15 is a perspective view of the securement system of FIG. 8 with a medical article positioned above the securement system, and shows the securement device disengaged from the latch.

In order to secure a medical article 60 to a patient using the securement system 80, the base 90 is attached to the patient, such as to the patient's skin, at a location where the medical article 60 is to be located, as shown in FIG. 15. As described above, the base 90 can be attached by the adhesive 92, sutures, or can be merely taped down.

Figure 16:
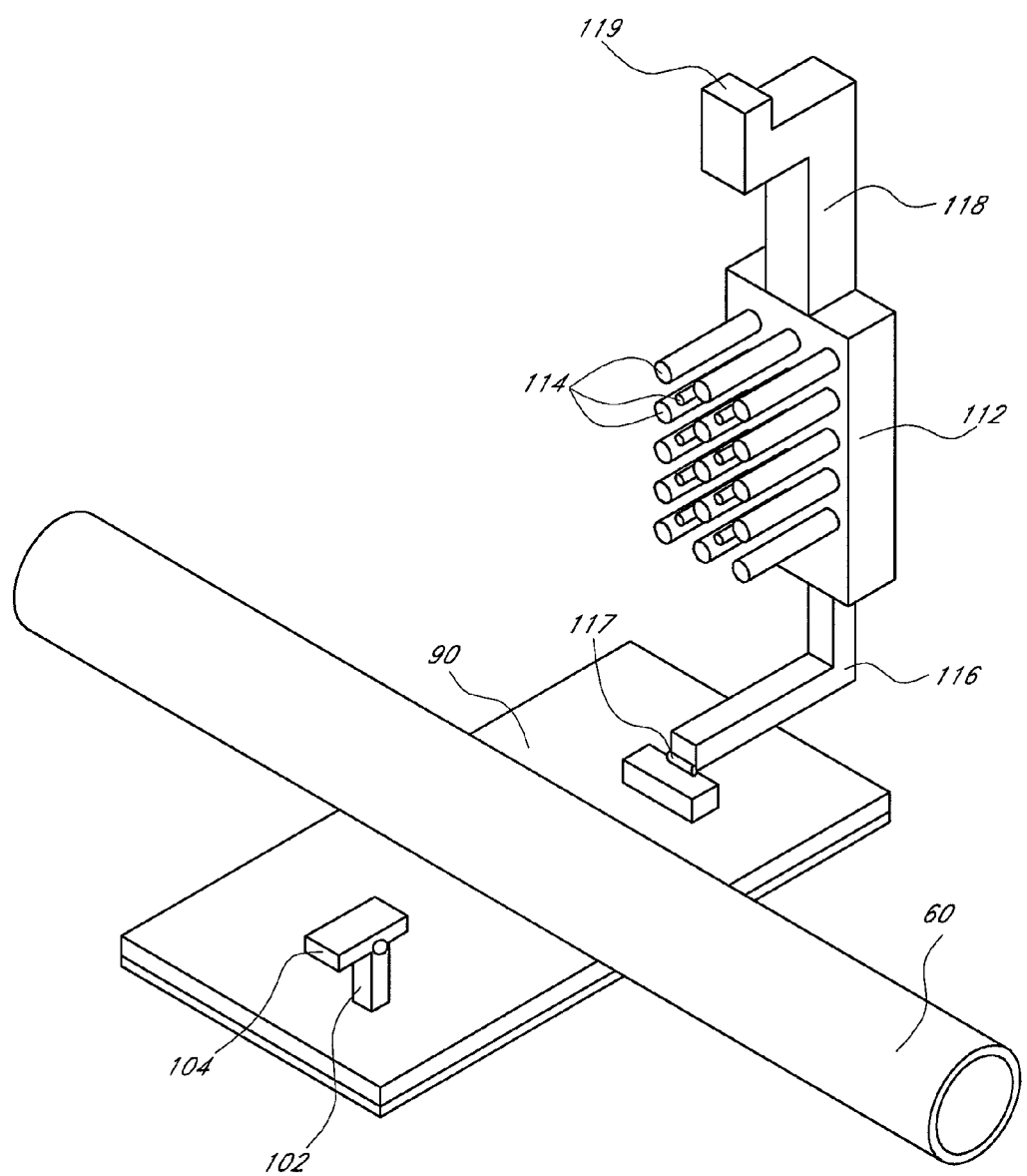
FIG. 16 is a perspective view of the securement system of FIG. 8 with the medical article positioned on the base, and shows the securement device disengaged from the latch.

Following attachment of the base 90, the medical article 60 can be placed above the securement system 80 while the securement device 110 is in the open position, as further shown in FIG. 16. Then, the medical article 60 is lowered onto the base 90, as shown in FIG. 16.

Figure 17:
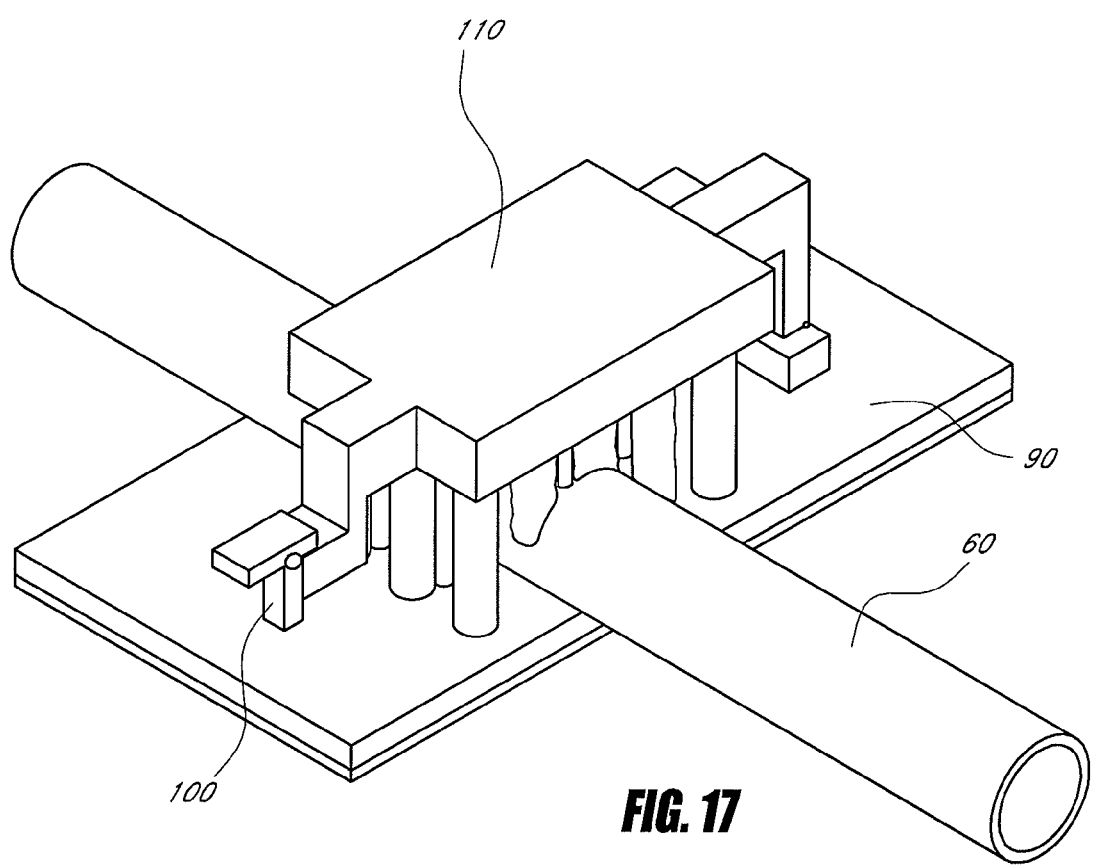
FIG. 17 is a perspective view of the securement system of FIG. 8 secured about the medical article.

The hinged member 116 is thereafter pivoted about the hinged section 117 to swing the securement device 110 in place over the medical article 60. When the securement device 110 is thus lowered over the medical article 60 into the closed position, the securement device 110 is engaged with the latch 100, thereby inhibiting movement of the securement device 110, as shown in FIG. 17. The securement device 110 presses against the medical article 60, and certain ones of the tentacles 114 deform and may conform to the medical article 60. Thus, the medical article 60 is secured by the application of pressure. Additional securement can be provided by applying an adhesive tape over the securement system 80.

Those of skill in the art will appreciate that the securement system 80 allows a healthcare provider easy access to the medical article 60 without excessive removal of tape or shifting of the medical article 60, while providing a secure, compressive force over the medical article 60. Those of skill in the art will also appreciate that the securement system 80 may cushion and protect the medical article 60 from external forces. The securement system 80 may additionally allow the tentacles 114 to provide a contaminant free contact surface, which allows air circulation and does not adhere to the medical article 60.

Those skilled in the art will appreciate additional advantages of the securement system 80. For example, the securement system 80 allows the medical article 60 to be secured, while adhesives that might gather contaminants are kept at a distance from a site at which the medical article might be inserted into the skin of the patient. The securement system 80 also allows the medical article 60 to be removed, adjusted, or replaced, such as with a similar medical article, with a medical article of a different size or shape, or with several medical articles. If the base 90 is omitted from the securement system 80, the securement device may be attached to the patient at a distance from a medical article and rotated down on top of the medical article, such as down on top of a wound dressing to provide pressure to the dressing.

Figure 18:
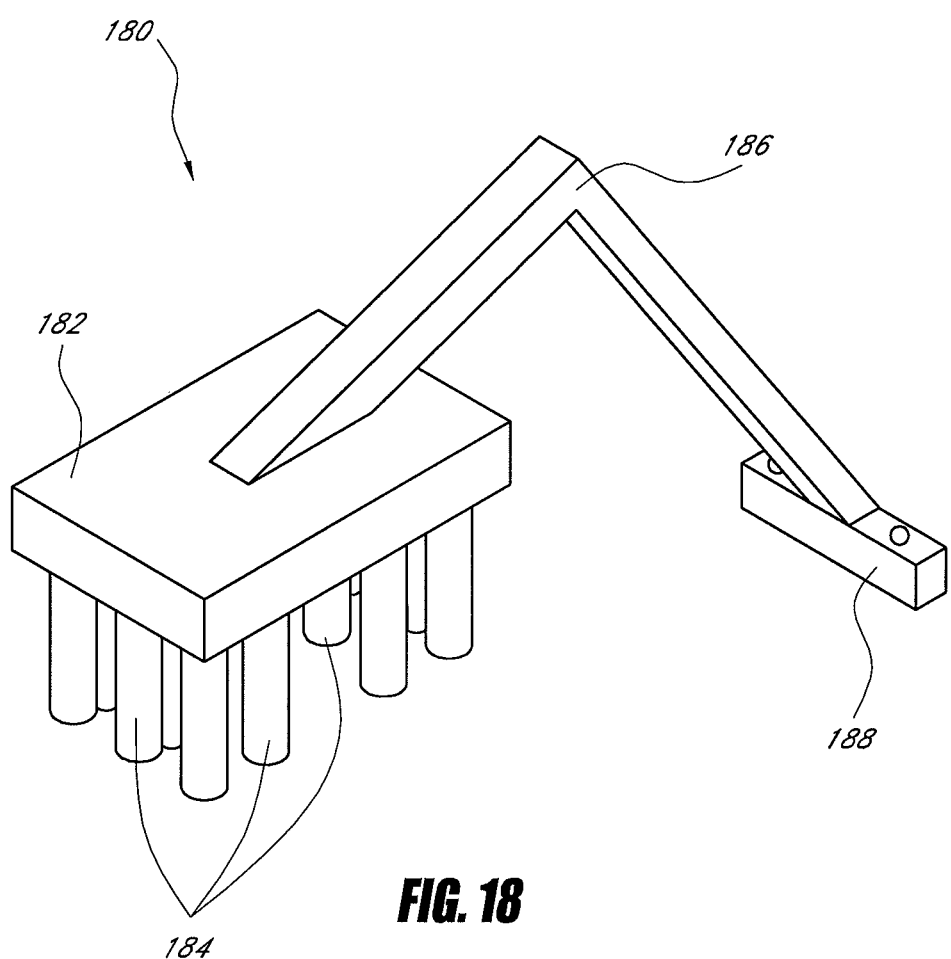
FIG. 18 is a perspective view of a securement device in accordance with another embodiment of the present invention and shows a support member connecting a body member to an attachment member.

With reference now to FIG. 18, an embodiment of a securement device 180 includes a body member 182, a plurality of tentacles 184, a support member 186, and an attachment member 188. The body member 182 may be configured similar to the body member 12 of the securement device 10. The tentacles 184 protrude from, or extend from, the body member 182. The support member 186 is attached to the body member 182, and the attachment member 188 is connected to the support member 186. The securement device 180 is configured to be placed over a medical article and secure the medical article to a patient, as described below in reference to FIGS. 23 and 24.

Figure 20:
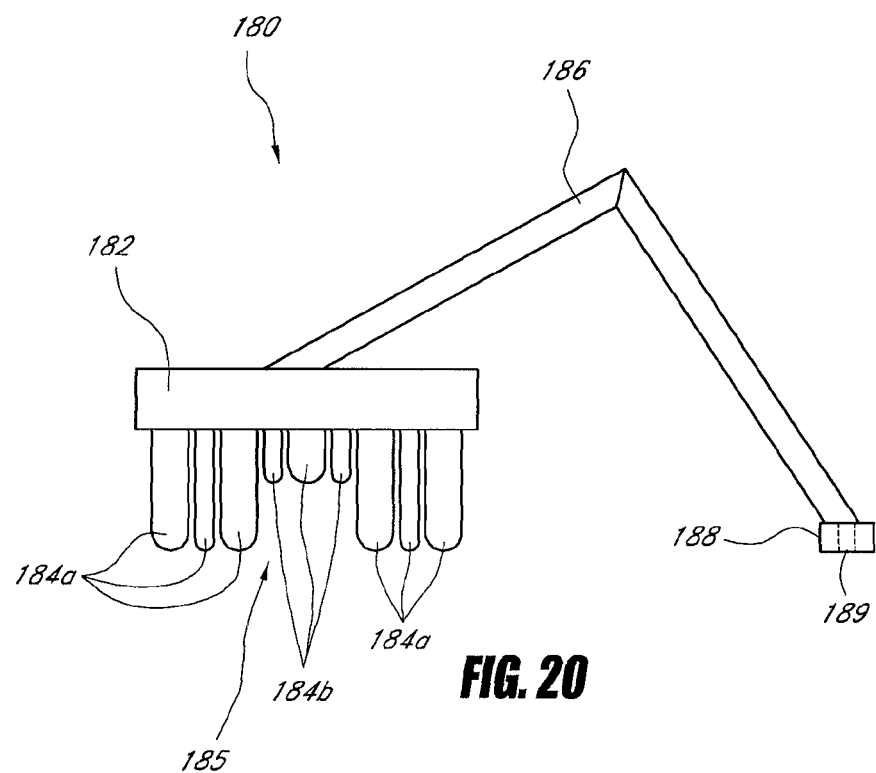
FIG. 20 is a front view of the securement device of FIG. 18.

As can be seen in a front view of the securement device 180 in FIG. 20, the tentacles 184 include a plurality of tentacles 184a, and a plurality of tentacles 184b shorter than the tentacles 184a. Of course, the plurality of tentacles 184 may have more than two different lengths The juxtaposition of the tentacles 184a with the tentacles 184b defines a receiving space 185 configured to accept at least a portion of a medical article, such as medical tubing. When a medical article is placed at least partially within the receiving space, certain ones of the tentacles 184b may compress and deform to provide transverse pressure on the medical article. In addition, certain ones of the tentacles 184a may surround a portion of the medical article or may additionally compress and deform.

When the securement device 180 is pressed down on the medical article, the pressure imposed by the tentacles 184b will be less than the pressure that would be applied if the tentacles 184b were the same length as the tentacles 184a. The shorter tentacles 184b need not compress as much to accept the medical article. Thus, the likelihood of occluding or impinging a medical article such as a medical tube or electrical wire may be reduced. In addition, pressing on the medical article with a combination of the tentacles 184a and the shorter tentacles 184b may apply a more even pressure to the medical article.

Although illustrated as defining a receiving space 185, the tentacles 184 may be configured as having substantially equivalent lengths to define a receiving surface. In addition, the tentacles 184 may be configured similar to the tentacles 14 of the securement device 10, illustrated in FIG. 1. Similarly, the tentacles 14 or the tentacles 114 of the securement device 110, illustrated in FIG. 11, may be configured to define one or more receiving spaces.

Figure 21:
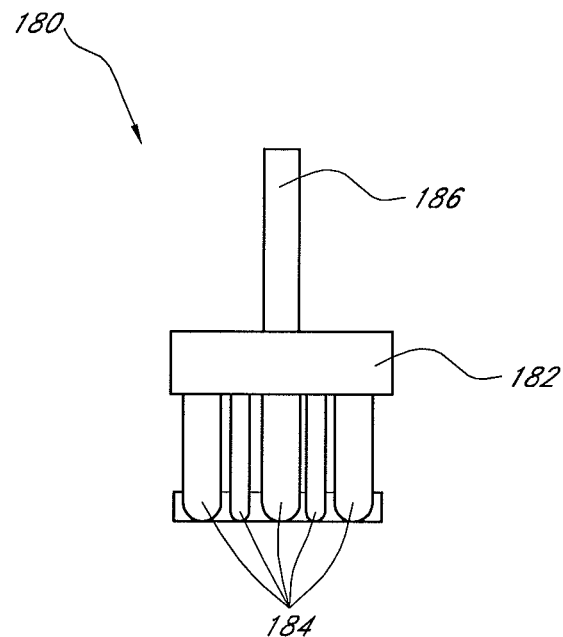
FIG. 21 is a side view of the securement device of FIG. 18, taken from the nearest side in FIG. 18.
Figure 22:
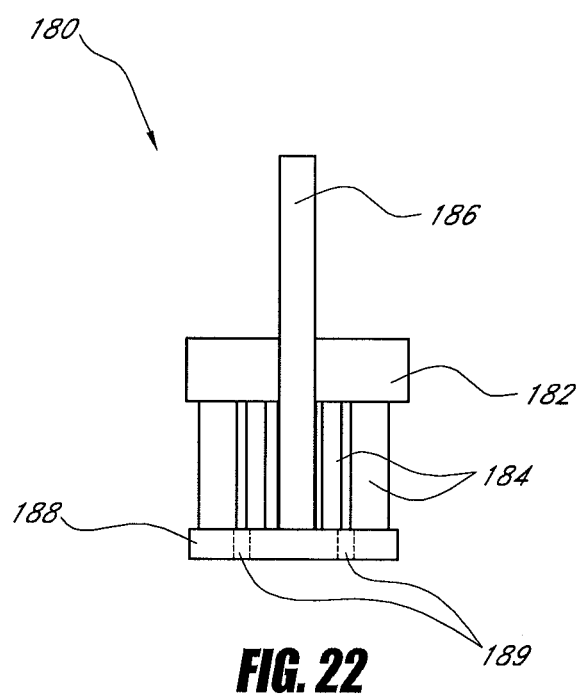
FIG. 22 is a side view of the securement device of FIG. 18 showing the support member.

The support member 186 supports the body member 182 when the attachment member 188 is mounted to a patient. In the illustrated embodiment, the support member 186 is angled. A portion of the support member 186 is transversely elevated over the body member 182 and attaches to the top of the body member 182, as shown in side views of the securement device 180 in FIGS. 21 and 22. In addition, the support member 186 is rigidly attached to or integrally formed with the attachment member 186 at an angle. When the attachment member 188 is mounted on the patient, the securement device 180 is pressed against the medical article by the support member 186, which is angled downwardly. In this way, the support member 186 naturally biases the body member 182 and the tentacles 184 toward the patient's skin. Of course, various modifications of the support are possible with a similar biasing effect.

The support member 186 may otherwise be configured similar to the hinged member 116 of the securement device 110, illustrated in FIG. 11. For example, the support member 186 may be fastened to the body member 182 in any number of ways including by use of adhesive, being integrally formed with the body member 182, or by use of a tongue and groove type joint. Similarly, the hinged member 116 from FIG. 11 may be shaped similar to the support member 186 and attached to the body member 112 on top of the body member 112.

Figure 19:
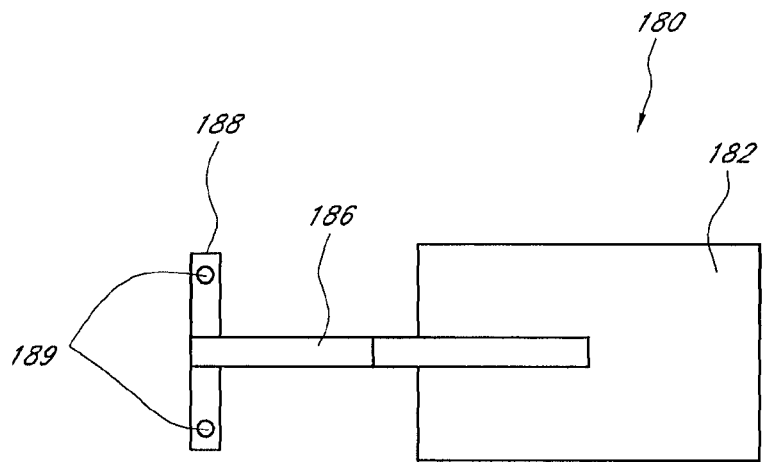
FIG. 19 is a top view of the securement device of FIG. 18.

The attachment member 188 is configured to be mounted to the patient. Thus, the attachment member 188 serves as a base for the securement device 180. As can be seen in a top view of the securement device 180 in FIG. 19, the attachment member 188 is illustrated as having one or more holes 189 formed through it. These holes may be used to suture the securement device 180 to the patient. The attachment member 188 may also be mounted on the patient by adhesive or tape, for example, or using any other means described above in relation to attaching the securement device 10 or the securement system 80 to the patient. Similarly, the securement system 80 may be mounted on the patient using sutures, and the hinged member 116 may be mounted on the patient using sutures when the base 90 is omitted from the securement system 80.

Those of skill in the art will understand that the securement device 180 may be constructed as a single piece or from a plurality of different pieces. For example, the complete securement device 180 may be formed by injection molding; or the body member 182, the tentacles 184, the support member 186, and the attachment member 188 may each be formed separately and thereafter joined together.

Figure 23:
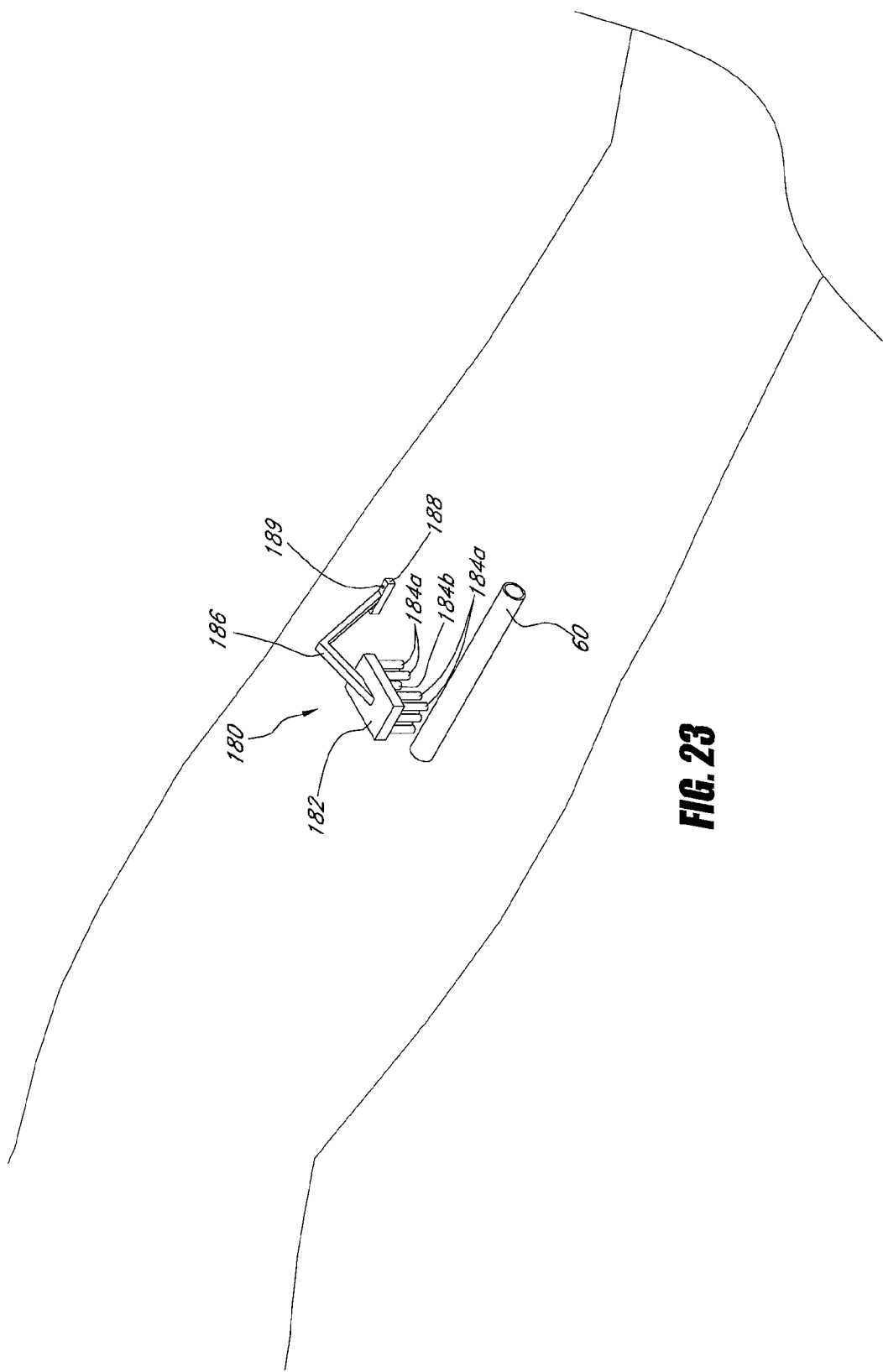
FIG. 23 is a perspective view of the securement device of FIG. 18 positioned above a medical article placed on a patient's skin.
Figure 24:
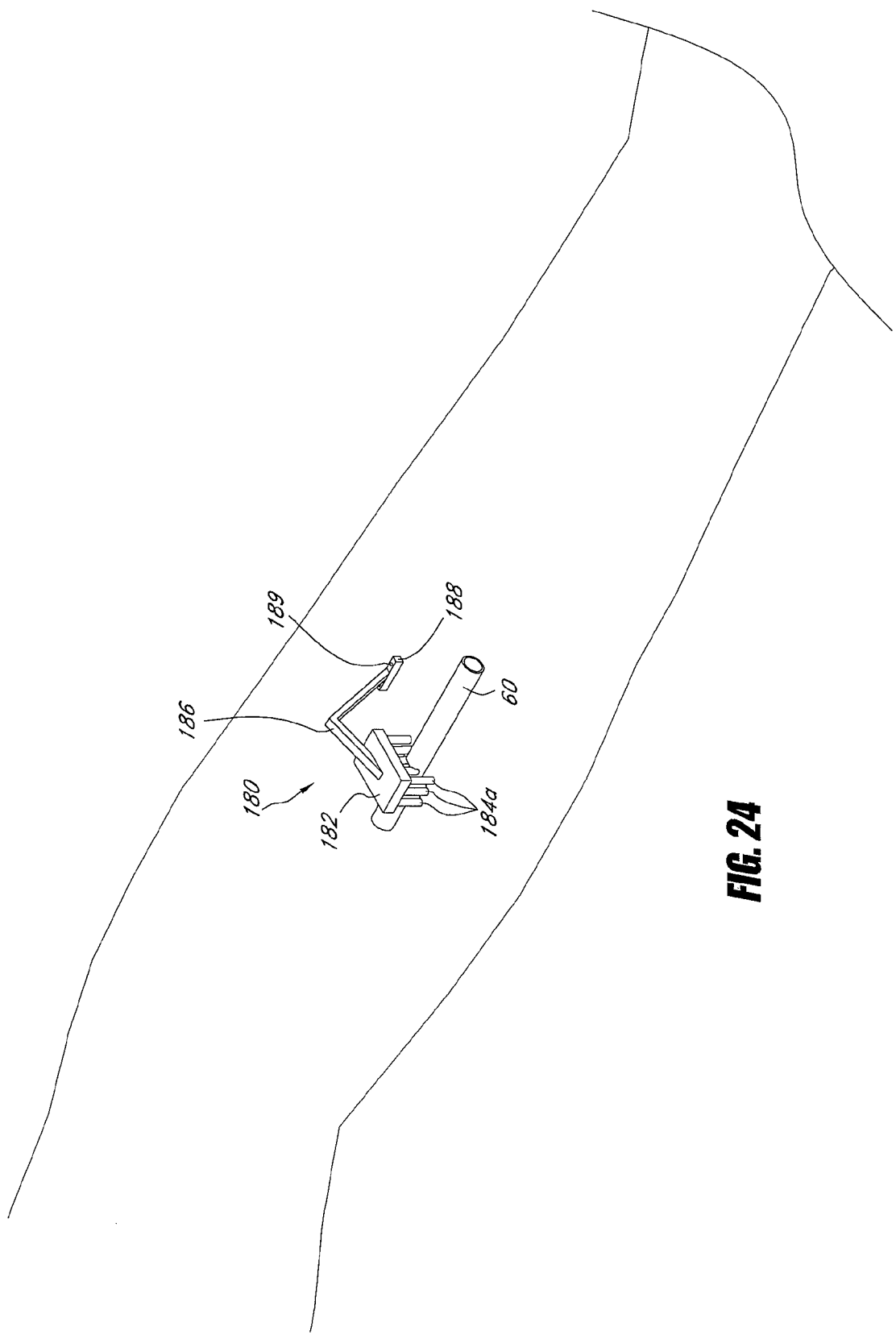
FIG. 24 is a perspective view of the securement device of FIG. 18 secured over the medical article.

A medical article 60 can be secured to a patient by the securement device 180, as shown in FIGS. 23 and 24. The medical article 60 is initially placed on a patient, such as against the skin of the patient. After placing the securement device 180 above the medical article 60, as shown in FIG. 23, a medical provider can then lower the securement device 180 over the medial article 60.

After the securement device has been lowered over the medical article 60, the medical provider can attach the securement device 180 to the patient by using sutures. The medical article 60 will thus be held on the patient by the securement device 180, as shown in FIG. 24, which is biased towards the patient by the support member 186.

Attaching the medical article 60 to the patient in this way not only arrests movement of the medical article 60, but also separates an area at which the securement is attached to the patient from an area at which the medical article 60 is located. The securement device 180 can be mounted using the attachment member 188, while securing the medical article 60 at a distance from the site of attachment. The biasing action of the support member 186 thus frees decreases the likelihood of interference with the medical article 60, as well as decreases the likelihood that contaminants will gather around the medical article 60.

The securement device 180 can hold a variety of medical articles, singularly or in combination, in position upon a patient. The securement device 180 allows a medical article to be removed, adjusted, or replaced, such as with a similar medical article, with a medical article of a different size or shape, or with several medical articles. To remove or reposition a medical article, the medical provider may remove or adjust the sutures or other fastening means or structure.

With reference now to FIG. 25, an embodiment of a securement system 250 includes an anchor pad 260 and a securement device 270. The securement device 270 is attached to an upper surface of the anchor pad 260. The anchor pad 260 may in turn be secured to a patient's skin. The securement system 250 is configured to be placed about a medical article and secure the medical article to the patient, as described below in reference to FIGS. 34 through 36.

Figure 26:
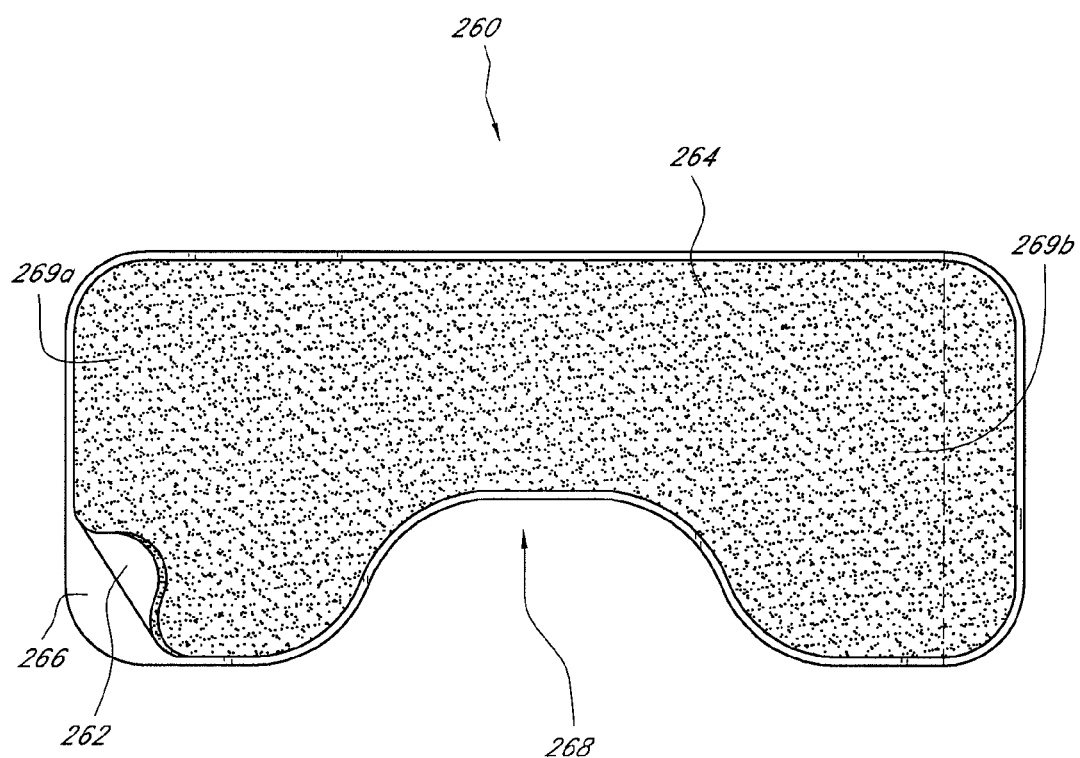
FIG. 26 is a top view of the anchor pad of FIG. 25.

FIG. 26 illustrates the anchor pad 260. The anchor pad 260 has a lower adhesive surface 262 which may adhere to the skin of a patient and an upper surface 264 configured to support the securement device 270. In combination, the lower adhesive surface 262, upper surface 264, and possibly one or more intermediate layers may comprise a laminate structure. A suitable laminate that comprises a foam or woven material with an adhesive layer is available commercially from Avery Dennison of Painsville, Ohio.

The lower adhesive surface 262 may be a medical-grade adhesive and can be either diaphoretic or nondiaphoretic, depending upon the particular application. The lower adhesive surface 262 may have additional types of medical adhesives laminated thereto. Although not illustrated, it will be understood that the anchor pad 260 can include suture holes in addition to the adhesive layer to further secure the anchor pad 260 to the patient's skin.

The upper surface 264 may comprise a foam (e.g., closed-cell polyethylene foam) or woven material (e.g., tricot) layer. A surface of the foam or woven material layer constitutes the upper surface 264 of the anchor pad 260. In the alternative, the upper surface 264 may comprise an upper paper or other nonwoven cloth layer, and an inner foam layer may be placed between the upper surface 264 and lower adhesive surface 262.

A removable paper or plastic release liner 266 may cover the lower adhesive surface 262 before use. The liner may resist tearing and be divided into a plurality of pieces to ease attachment of the anchor pad 260 to a patient's skin. The liner may be made of a paper, polyester, or similar material.

In the illustrated embodiment, the anchor pad 260 has a concave section 268 that narrows the center of anchor pad 260 where the securement device 270 attaches. As a result, the lateral sides of the anchor pad 260, illustrated as sections 269a and 269b, have more contact area which provides greater stability and adhesion to a patient's skin. Additionally, a medical article may be inserted into the patient's skin at a location nearer to the securement device 270 than if the concave section 268 were omitted. The anchor pad 260, however, is not limited to requiring the concave section 268. The anchor pad 260 may have any shape that allows attachment of the anchor pad 260 to a patient's skin and allows the securement device 270 to attach to the anchor pad 260.

In some embodiments, the anchor pad 260 is omitted from the securement system 250. In these embodiments, the securement device 270 may be attached to the patient in any number of ways previously described, such as using means described in reference to securing the base 90 of the securement system 80. For example, the securement device 270 could be attached to the patient using an adhesive or sutures, or by placing tape over the securement device 270.

FIGS. 27-33 illustrate the securement device 270 without the anchor pad 260. Preferably, the securement device 270 and the anchor pad 260 are packaged and delivered to the medical provider in an assembled state. Of course the medical provider could assemble one or more of the components of the securement system 250.

Figure 27:
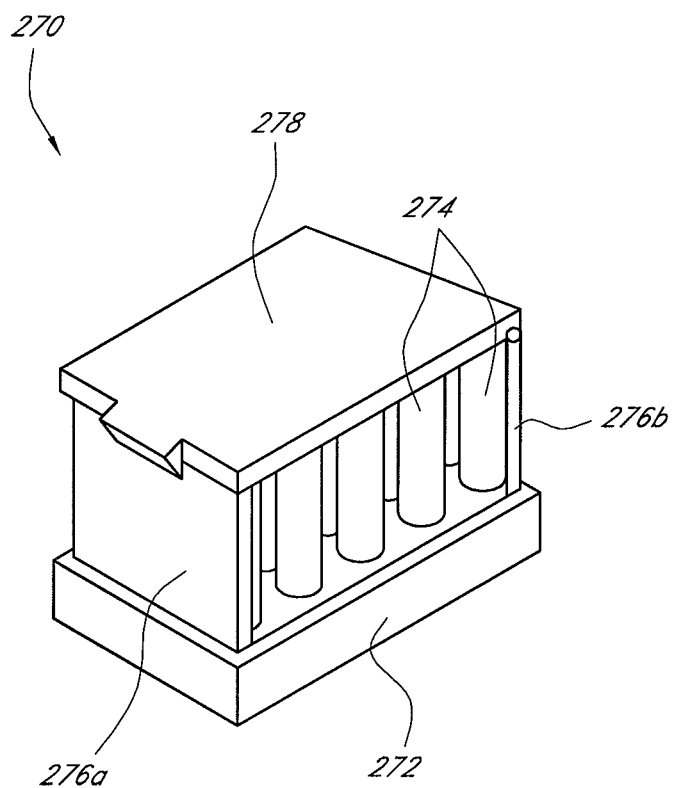
FIG. 27 is a perspective view of the securement device of FIG. 25, and shows side members and a top member.

As can be seen in a perspective view of the securement device 270, as illustrated in FIG. 27, the securement device 270 includes a body member 272, a plurality of tentacles 274, side members 276a and 276b, and a top member 278. The plurality of tentacles 274 can extend from the body member 272 or from the top member 278. A portion of the plurality of tentacles 274 can extend from the body member 272 while another portion of the plurality of tentacles 274 extend from the top member 278. In the illustrated embodiment, the top member 278 is secured over the tentacles 274. The top member 274 engages and is secured by the side member 276a, while being supported by the side member 276b.

The body member 272 is disposed beneath the tentacles 274. The tentacles 274 protrude above, or extend above, the body member 272. Thus, a medical article can be secured above the body member 272. The body member 272 may otherwise be configured similar to any of the body members 12, 112, or 118 of the securement devices 10, 110, or 180, respectively.

In the illustrated embodiment, the tentacles 274 form a compressible receiving surface 275 that a medical article may rest on. The receiving surface 275 may, for example, be defined similar to the receiving surface 16 illustrated in FIG. 4. The receiving surface 275 may or may not be substantially planar. In some embodiments, the receiving surface 275 is configured as a plane that forms an acute angle with the body member 272 and/or the anchor pad 260. Such angled receiving surface imparts an angular orientation to the medical article relative to the patient's skin, and may be selected based on the intended application of the securement device 270. The tentacles 274 may otherwise be configured similar to any of the tentacles 14, 114, or 184 of the securement devices 10, 110, or 180, respectively.

The side members 276a and 276b are disposed on opposing sides of the tentacles 274. The side members 276a and 276b are illustrated as planar members covering respective sides of the securement device 270, as shown in front views of the securement device 270 and side views of the securement device 270, illustrated in FIGS. 28 and 29, and FIGS. 32 and 33, respectively. The side members are also illustrated as being connected to an upper surface of the body member 272. The side members 276a and 276b, however, are not limited to this configuration. The side members 276a and 276b may each be configured to cover only a portion of a respective side of the securement device 270 or may each have a shape other than planar. The side members may be connected a side surface of the body member 272 or implemented separate from the body member 272.

Figure 28:
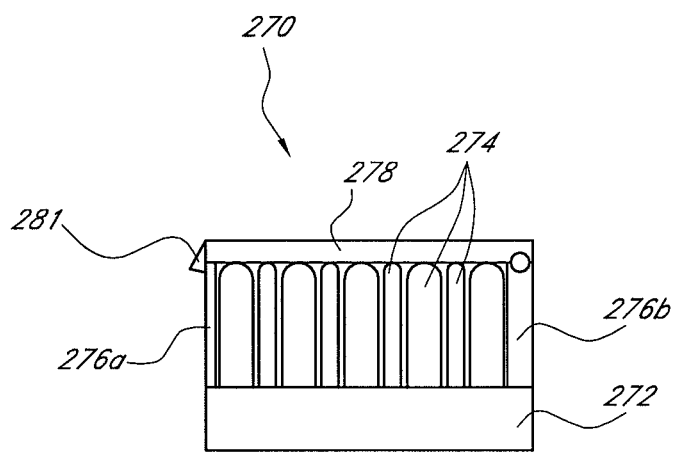
FIG. 28 is a front view of the securement device of FIG. 27, and shows the top member engaged with one of the side members and in a closed position.
Figure 29:
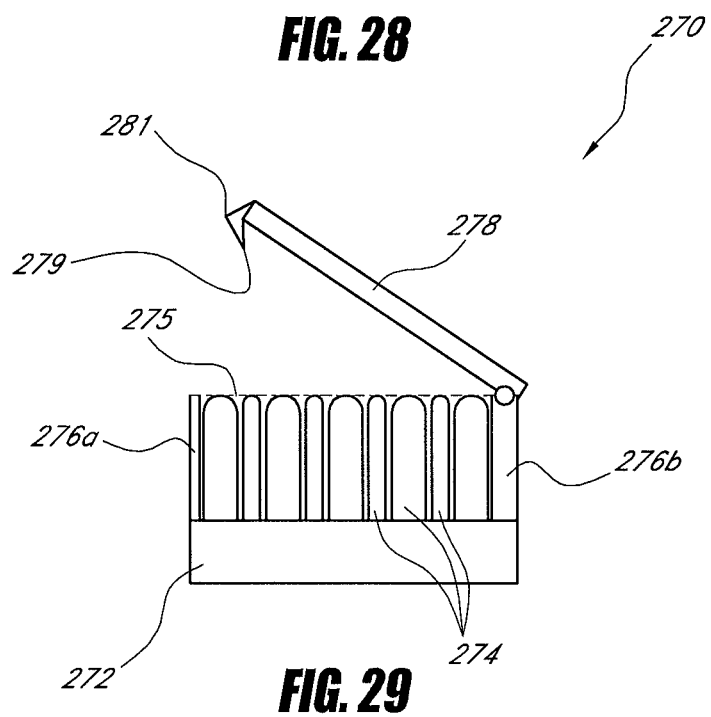
FIG. 29 is another front view of the securement device of FIG. 27, and shows the top member disengaged from the one side member and in an open position.
Figure 30:
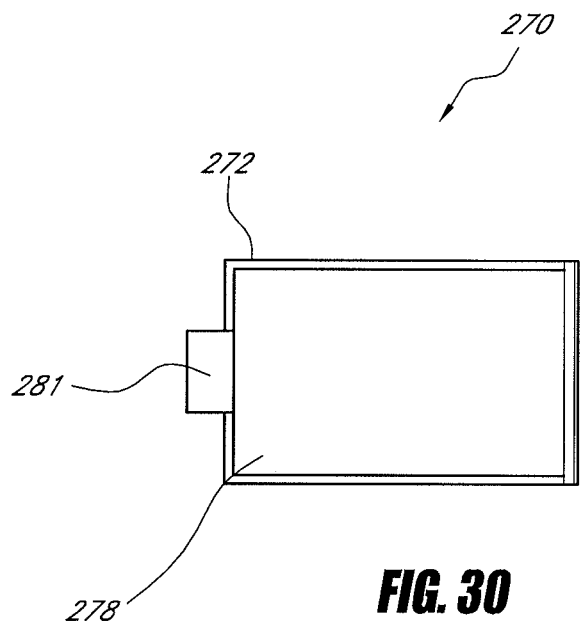
FIG. 30 is a top view of the securement device of FIG. 27, and shows the top member engaged with the one side member and in a closed position.
Figure 31:
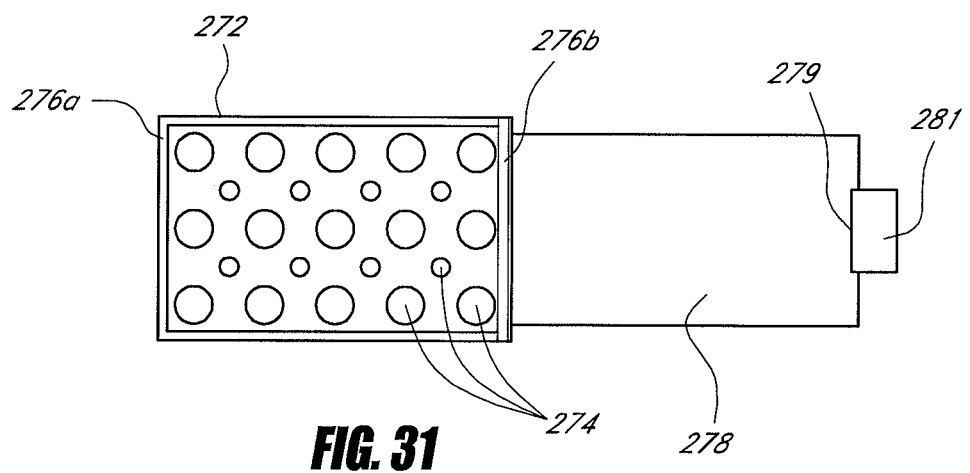
FIG. 31 is another top view of the securement device of FIG. 27, and shows the top member disengaged from the one side member and in the open position.
Figure 32:
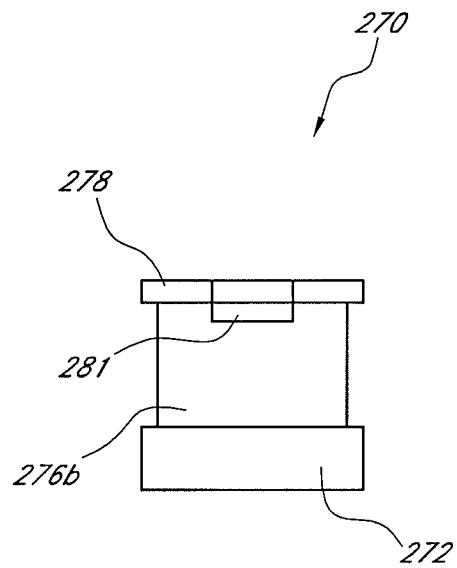
FIG. 32 is a side view of the securement device of FIG. 27 and shows a latching mechanism.
Figure 33:
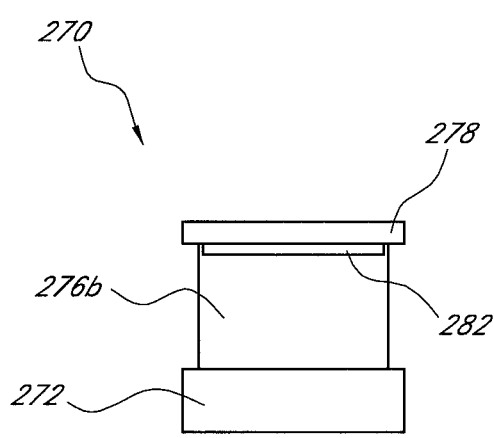
FIG. 33 is side view of the securement device of FIG. 27 and shows a hinge mechanism.

Similarly, the top member is illustrated as a planar member covering the top of the tentacles 274 (i.e. covering the tops of substantially all of the tentacles 274), as shown in a side view of the securement device 270 and a top view of the securement device 270, illustrated in FIGS. 28 and 30, respectively. The top member 278, however, is not limited to this configuration. The top member 278 may be configured to cover only a portion of the top of the securement device 270, to cover the tops of only some of the tentacles 274, or to have a shape other than planar. In some embodiments, the top member 278 is angled to correspond to a receiving surface with an angular orientation.

The side members are made of a relatively stiff material, such as medically compatible plastics, polymers, or composites. The side member 276b is illustrated as supporting the top member 278 by a hinge 282. The hinge 282 may be any number of hinges described above in reference to the hinged member 116 of the securement device 110, illustrated in FIG. 11. The side member 276a is illustrated as being configured to engage and secure the top member 278.

Figure 34:
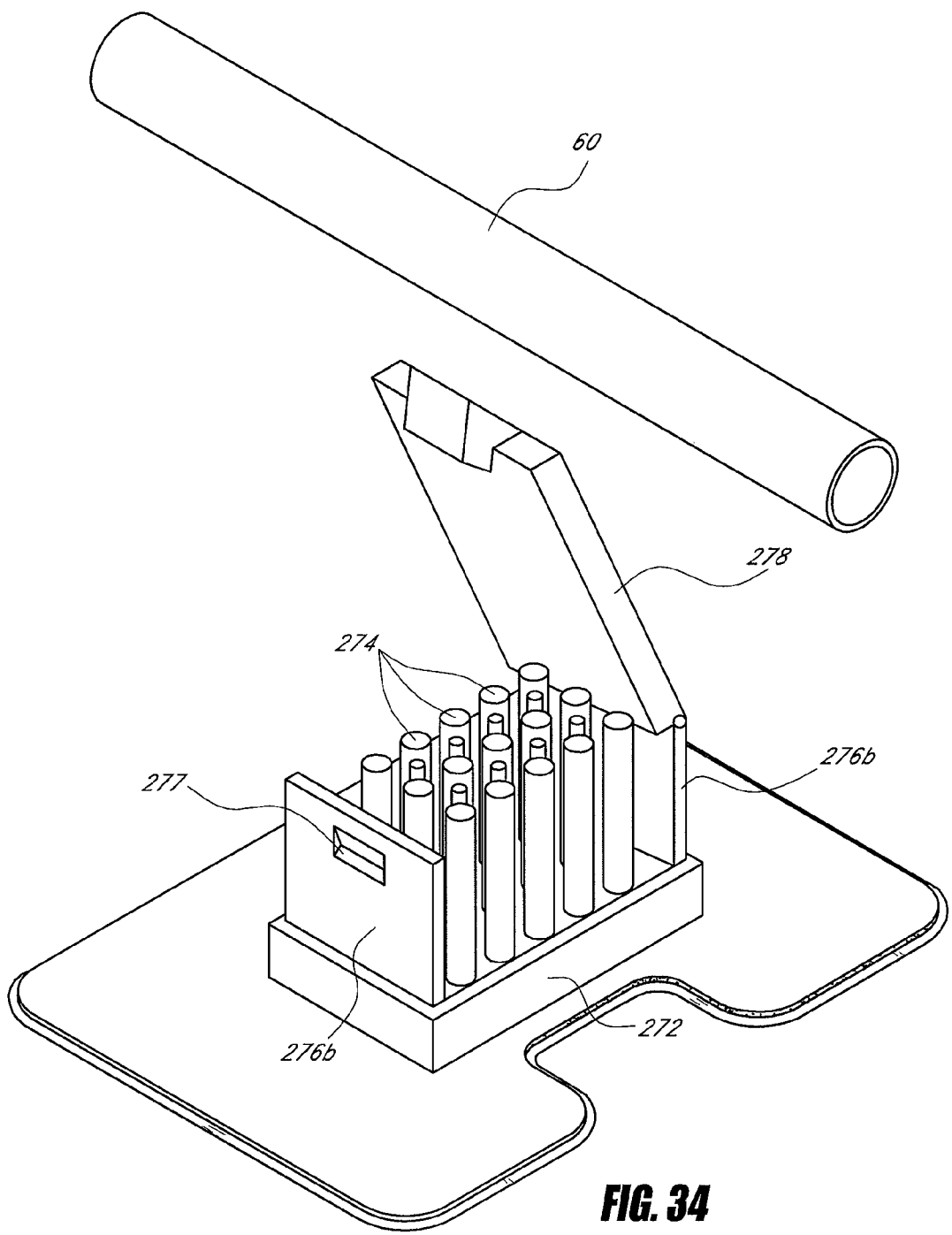
FIG. 34 is a perspective view of the securement system of FIG. 25 with a medical article positioned above the securement system, and shows the top member disengaged from the one side member.
Figure 35:
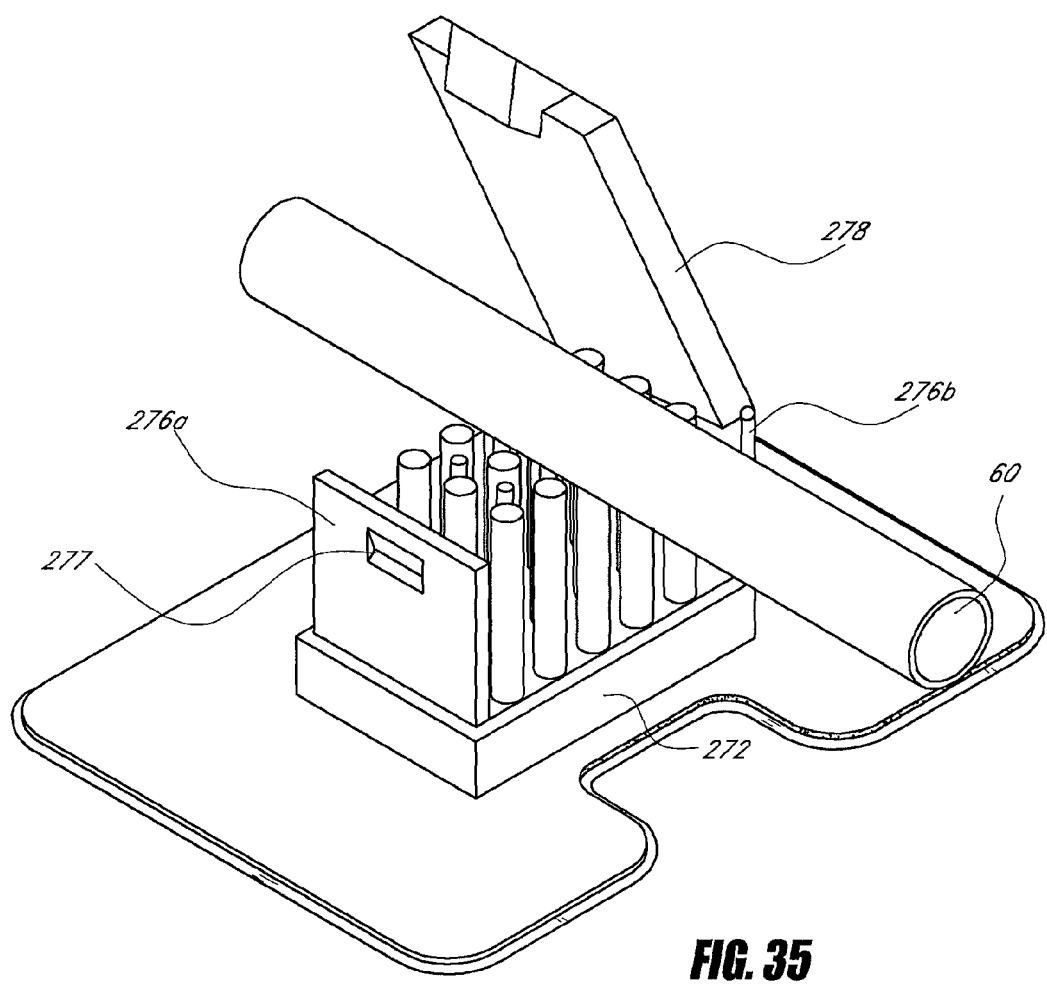
FIG. 35 is a perspective view of the securement system of FIG. 25 with the medical article positioned on the securement system, and shows the top member disengaged from the one side member.
Figure 36:
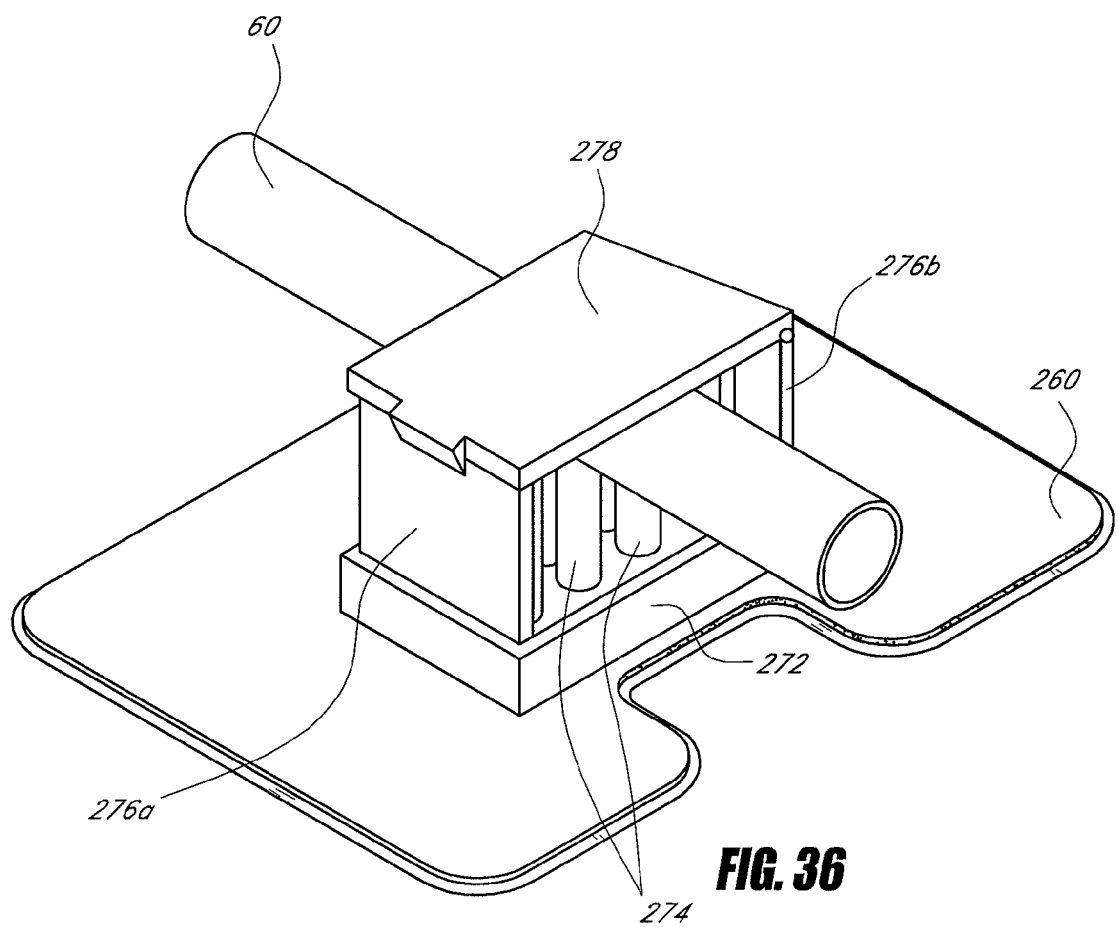
FIG. 36 is a perspective view of the securement system of FIG. 25 secured about the medical article with the top member in the closed position.

In order to engage the top member 278, the side member 276a is configured to define a depression 277 therein, as can be seen in FIGS. 34 and 35. The top member 278 has a corresponding protrusion 279 configured to latch into the depression 277 and thereafter maintain a substantially secure connection. Thus, the top member 278 can engage with the side member 276a, thereby securing the top member 278 to the side member 276a. Those skilled in the art will appreciate that other engagement mechanisms not herein described may additionally or instead be used.

When the top member is rotated down over the tentacles 274 and pressure applied, the top member 278 will engage the side member 276a and cover at least some of the tentacles 274, as shown in a side view of the securement device 270 and a top view of the securement device 270, illustrated in FIGS. 28 and 30, respectively. In this closed configuration, a portion of a medical article can be secured between the top member 278 and the tentacles 274. Certain ones of the tentacles will compress and deform in response to the medical article, thereby providing adequate space between the top member 278 and the tentacles 274 to accept the medical article, while still providing sufficient pressure to inhibit movement of the medical article and not substantially occlude flow through the medical article.

When transverse pressure away from the tentacles 274 is applied to a protrusion 281 on the top member 278, the top member 278 will disengage from the side member 276a. The top member can then be rotated up into an open position to expose the tentacles 274, as shown in a side view of the securement device 270 and a top view of the securement device 270, illustrated in FIGS. 29 and 31, respectively. The top member 278 and the side member 276a may of course be configured to engage in any other way or using any other means that will secure the top member 278 over at least a portion of the tentacles 274.

In some embodiments, one or more of the side members 276a and 276b and the top member 278 are omitted from the securement system 270. In certain of these embodiments, the top member 278 is configured to cover at least a portion of the top of the securement device 270 using other means. For example, the top member 278 may have a generally L-shaped or inverted U-shaped configuration and be hinged to the body member 272. As another example, the side members 276a and 276b, and the top member 278 may all be omitted. In these embodiments, an adhesive tape may be applied over a medical article placed on top of the securement device 270 to secure the medical article, or the tentacles 274 may comprise an adhesive configured to inhibit movement of the medical article when contacting the medical article, for example.

Those of skill in the art will understand that the securement device 270 may be constructed as a single piece or from a plurality of different pieces. For example, the complete securement device 270 may be formed by injection molding; or the body member 272, the tentacles 274, the sidewalls 276a and 276b, and the top member 278 may each be formed separately and thereafter joined together.

In order to secure a medical article 60 to a patient using the securement system 250, the anchor pad 260 is attached to the patient, such as to the patient's skin, at a location where the medical article 60 is to be located, as shown in FIG. 34. As described above, the anchor pad 260 can be attached by adhesive, sutures, or can be merely taped down.

Following attachment of the anchor pad 260, the medical article 60 can be placed above the securement system 250 while the securement device 270 is in the open position, as further shown in FIG. 34. Then, the medical article 60 is lowered onto the securement device 270 to rest on the tops of the tentacles 274, as shown in FIG. 35.

The top member 278 is thereafter rotated down over the medical article 60 and over the tentacles 274. When the top member 278 is thus lowered over the medical article 60 and the tentacles 274 into the closed position, pressure is applied to the top member 278 to engage the top member 278 with the side member 276b, as shown in FIG. 35. The top member 278 presses the medical article 60 against some of the tentacles 274, and certain ones of the tentacles 274 deform and may conform to the medical article 60. Thus, the medical article 60 is secured by the application of pressure. Additional securement can be provided by applying an adhesive tape over the securement device 270.

It is to be understood that not necessarily all objects or advantages disclosed herein may be achieved in accordance with any particular embodiment. Thus, for example, those skilled in the art will recognize that embodiments may be carried out in a manner that achieves or optimizes one advantage or group of advantages as taught herein without necessarily achieving other objects or advantages as may be taught or suggested herein. In addition to the variations described herein, other known equivalents for each feature can be incorporated by one of ordinary skill in this art to construct a device and/or system in accordance with principles of this invention.

While the illustrative embodiments have been described with particularity, it will be understood that various other modifications will be apparent to and can be readily made by those skilled in the art without departing from the spirit and scope of the invention. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but by a fair reading of the claims that follow.

What is claimed is:

1. A device for securing a medical article to a patient, comprising:
   a body member; and
   a plurality of tentacles extending from the body member and being arranged in a two dimensional array of rows and columns, each column and row including two or more tentacles, one or more of the plurality of tentacles being configured to bend in at least a lateral direction at least when the device is pressed against the medical article so as to surround and form a friction fit with a portion of the medical article, at least one of the plurality of tentacles being moveable independent of another of the plurality of tentacles at least when the device is pressed against the medical article.

2. The device of claim 1, wherein the plurality of tentacles are formed of anti-microbial material.

3. The device of claim 1, wherein the device is formed of a material chosen from plastic, polymer, silicone, polyurethane, natural rubber, and synthetic rubber.

4. The device of claim 1, wherein the body member and the plurality of tentacles are integrally molded.

5. The device of claim 1, wherein each of the plurality of tentacles is an elongated protrusion formed of resilient material.

6. The device of claim 1, further comprising a connection member that secures the device against the medical article.

7. The device of claim 1, further comprising an adhesive, the adhesive being disposed on the device so as to adhere the device to the patient.

8. The device of claim 7, wherein the adhesive is disposed on the plurality of tentacles.

9. The device of claim 1, further comprising:
a base having a surface for mounting to the patient; and
a support member coupling the base to the body member so as to allow the body member to move with respect to the base.

10. The device of claim 9, further comprising a hinge between the base and the support member.

11. The device of claim 9, further comprising a biasing element configured to lock the support member in place.

12. A system for securing a medical article to a patient, comprising:
a medical article having an elongated body extending generally along a longitudinal axis; and
a retainer comprising:
an anchor pad having a lower surface at least partially covered by an adhesive for contacting the patient's skin;
a body member supported by the anchor pad; and
a plurality of pliant fingers extending from the body member and being configured to deform when pressed against the medical article, at least one of the plurality of pliant fingers being configured to bend in at least a lateral direction and a longitudinal direction so as to surround and form a friction fit with a portion of the medical article, at least one of the plurality of pliant fingers being moveable independent of another of the plurality of pliant fingers at least when pressed against the medical article,
wherein the medical article extends beyond an extremity of the body member in both longitudinal directions at least when the anchor pad is adhered to the patient's skin.

13. The system of claim 12, wherein the body member is connected to the anchor pad by a support member.

14. A securement device comprising:
an adhesive layer configured to attach the device to a patient;
a lower member supported by the adhesive layer;
an upper member being moveable with respect to the lower member between an open position in which at least a portion of a receiving area is exposed and a closed position in which the portion of the receiving area is covered; and
a plurality of tentacles each having a tip, the plurality of tentacles being configured to at least initially apply pressure to a secured medical article at a plurality of noncontiguous locations, the plurality of noncontiguous locations being spaced apart along a lateral axis, at least a portion of the plurality of tentacles being compressible when the upper member is in the closed position and the secured medical article is disposed in the receiving area, wherein a length of one or more of the plurality of tentacles is greater than a diameter of the secured medical article, wherein one or more of the plurality of tentacles are configured to bend in at least a lateral direction and a longitudinal direction so as to surround and form a friction fit with a portion of the secured medical article, and wherein at least one tip is moveable independent of another tip at least when the upper member is moved into the closed position.

15. The device of claim 14, wherein the upper member is a body member.

16. The device of claim 14, wherein the lower member is a base.

17. The device of claim 14, further comprising a support member coupling the lower member to the upper member.

18. The device of claim 17, wherein the upper member is coupled to the lower member when in the open and closed positions.

19. The device of claim 14, further comprising a hinge disposed so that the upper member is movably coupled to the lower member.

20. The device of claim 14, further comprising a biasing element configured to selectively limit movement of the upper member towards the open position.

21. A device for securing a medical article to a patient, comprising:
an anchor pad having an upper surface and a lower surface, the lower surface including an adhesive layer on at least a portion thereof;
a retainer supported by the anchor pad and capable of receiving a portion of the medical article, the retainer including:
a lower member having first and second sides, and a receiving area disposed therebetween;
an upper member having a first side and a second side, the first side of the upper member being attached to the first side of the lower member, and the second side of the upper member being moveable between a closed position, in which the second side of the upper member lies generally above the second side of the lower member, and an open position, in which the second side of the upper member is spaced apart from the second side of the lower member so as to expose the receiving area on the lower member;
a plurality of tentacles each terminating in a tip, the plurality of tentacles corresponding in position to the receiving area in the lower member when the upper member lies in the closed position, at least a portion of the plurality of tentacles being compressible when the upper member is in the closed position and the portion of the medical article is disposed in the receiving area such that the plurality of tentacles surround an arc of at least 180° of the portion of the medical article without substantially compressing the medical article, wherein a first tentacle of the plurality of tentacles is disposed on the retainer so as to be laterally offset from a second tentacle of the plurality of tentacles, the first tentacle bendable in at least a lateral direction and a longitudinal direction so as to form a friction fit with the portion of the medical article, wherein a third tentacle of the plurality of tentacles is disposed on the retainer so as to be longitudinally offset from the second tentacle, and wherein the tip of at least one of the plurality of tentacles is moveable independent of the tip of another of the plurality of tentacles at least when the upper member is moved into the closed position;
a support member coupling the lower member to the upper member; and
a biasing element configured to selectively limit movement of the upper member towards the open position.

* * * * *